United States Patent
Jung et al.

(10) Patent No.: US 10,745,362 B2
(45) Date of Patent: Aug. 18, 2020

(54) HETEROCYCLIC COMPOUND AND ORGANIC LIGHT EMITTING DEVICE COMPRISING SAME

(71) Applicant: LG CHEM, LTD., Seoul (KR)

(72) Inventors: Min Woo Jung, Daejeon (KR); Dong Hoon Lee, Daejeon (KR); Jungoh Huh, Daejeon (KR); Boonjae Jang, Daejeon (KR); Minyoung Kang, Daejeon (KR); Dong Heo, Daejeon (KR); Miyeon Han, Daejeon (KR)

(73) Assignee: LG CHEM, LTD., Seoul (KR)

( * ) Notice: Subject to any disclaimer, the term of this patent is extended or adjusted under 35 U.S.C. 154(b) by 142 days.

(21) Appl. No.: 15/567,276

(22) PCT Filed: May 13, 2016

(86) PCT No.: PCT/KR2016/005087
§ 371 (c)(1),
(2) Date: Oct. 17, 2017

(87) PCT Pub. No.: WO2016/182388
PCT Pub. Date: Nov. 17, 2016

(65) Prior Publication Data
US 2018/0127385 A1    May 10, 2018

(30) Foreign Application Priority Data
May 14, 2015  (KR) .......................... 10-2015-0067298

(51) Int. Cl.
| H01L 51/50 | (2006.01) |
| C07D 251/24 | (2006.01) |
| C09K 11/06 | (2006.01) |
| C07D 239/24 | (2006.01) |
| C07D 251/12 | (2006.01) |

(Continued)

(52) U.S. Cl.
CPC .......... *C07D 251/24* (2013.01); *C07D 239/24* (2013.01); *C07D 239/26* (2013.01); *C07D 251/12* (2013.01); *C07D 403/10* (2013.01); *C07D 405/10* (2013.01); *C07D 409/10* (2013.01); *C09K 11/06* (2013.01); *H01L 51/0067* (2013.01); *H01L 51/50* (2013.01);
(Continued)

(58) Field of Classification Search
None
See application file for complete search history.

(56) References Cited

U.S. PATENT DOCUMENTS

| 2004/0137270 A1 | 7/2004 | Seo et al. |
| 2014/0054559 A1 | 2/2014 | Kim et al. |
| 2014/0175395 A1 | 6/2014 | Kim et al. |

FOREIGN PATENT DOCUMENTS

| JP | 2004204238 A | 7/2004 |
| JP | 2010245060 A | 10/2010 |

(Continued)

OTHER PUBLICATIONS

Sukegawa, et al.: "Large Electronic Coupling in a Homoconjugated Donor-Acceptor System Involving Carbon-bridged Oligo(p-phenylenevinylene) and Triazine", XP-003034333, Chemistry Letters, vol. 43, No. 5, Jan. 1, 2014, pp. 699-701.

*Primary Examiner* — Gregory D Clark
(74) *Attorney, Agent, or Firm* — Dentons US LLP

(57) ABSTRACT

The present specification provides a hetero-cyclic compound and an organic light emitting device comprising the same.

15 Claims, 1 Drawing Sheet

(51) Int. Cl.
*C07D 239/26* (2006.01)
*C07D 403/10* (2006.01)
*C07D 405/10* (2006.01)
*C07D 409/10* (2006.01)
*H01L 51/00* (2006.01)

(52) U.S. Cl.
CPC ................ *C09K 2211/1044* (2013.01); *C09K 2211/1059* (2013.01)

(56) References Cited

FOREIGN PATENT DOCUMENTS

| | | | | |
|---|---|---|---|---|
| KR | 10-2014-0015226 A | 2/2014 | | |
| KR | 10-2014-0080205 A | 6/2014 | | |
| KR | 10-2014-0128878 A | 11/2014 | | |
| KR | 10-2014-0145965 A | 12/2014 | | |
| KR | 10-2015-0034390 A | 4/2015 | | |
| KR | 10-2015-0066202 A | 6/2015 | | |
| KR | 10-20140037907 | * 10/2015 | ........... | C07D 307/91 |
| KR | 10-2016-0041018 A | 4/2016 | | |
| KR | 2016041018 | * 4/2016 | ........... | C07D 333/50 |
| WO | 2015/046955 A1 | 4/2015 | | |
| WO | 2015046955 A1 | 4/2015 | | |
| WO | 2015061198 A1 | 4/2015 | | |
| WO | 2015/084114 A1 | 6/2015 | | |
| WO | 2017/171375 A1 | 10/2017 | | |

* cited by examiner

[Figure 1]
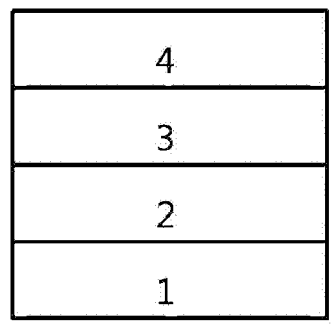
[Figure 2]
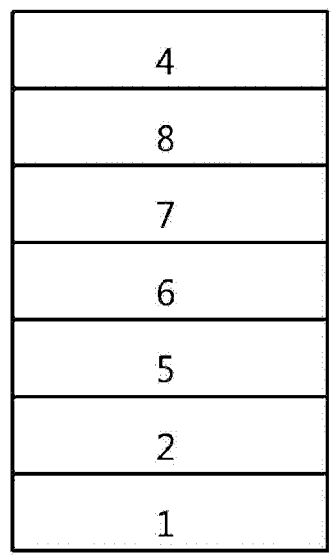

HETEROCYCLIC COMPOUND AND ORGANIC LIGHT EMITTING DEVICE COMPRISING SAME

TECHNICAL FIELD

This application is a National Stage Entry of International Application No. PCT/KR2016/005087, filed on May 13, 2016, and claims the benefit of and priority to Korean Application No. 10-2015-0067298, filed on May 14, 2015, all of which are hereby incorporated by reference in their entirety for all purposes as if fully set forth herein.

The present specification relates to a hetero-cyclic compound and an organic light emitting device comprising the same.

BACKGROUND ART

In general, an organic light emitting phenomenon refers to a phenomenon in which electric energy is converted into light energy by using an organic material. An organic light emitting device using the organic light emitting phenomenon usually has a structure including a positive electrode, a negative electrode, and an organic material layer interposed therebetween. Here, the organic material layer may have a multilayered structure composed of different materials in order to improve the efficiency and stability of an organic light emitting device in many cases, and for example, may be composed of a hole injection layer, a hole transporting layer, a light emitting layer, an electron transporting layer, an electron injection layer, and the like. In the structure of the organic light emitting device, if a voltage is applied between two electrodes, holes are injected from a positive electrode into the organic material layer and electrons are injected from a negative electrode into the organic material layer, and when the injected holes and electrons meet each other, an exciton is formed, and light is emitted when the exciton falls down again to a ground state.

There is a continuous need for developing a new material for the aforementioned organic light emitting device.

CITATION LIST

Patent Document

Official Gazette of Korean Patent Application Laid-Open No. 2000-0051826

DETAILED DESCRIPTION OF THE INVENTION

Technical Problem

The present specification describes a hetero-cyclic compound and an organic light emitting device comprising the same.

Technical Solution

An exemplary embodiment of the present specification provides a hetero-cyclic compound represented by the following Chemical Formula 1.

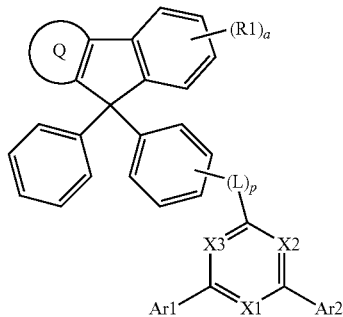

[Chemical Formula 1]

In Chemical Formula 1,

X1 to X3 are the same as or different from each other, and are each independently CR or N, Q is a substituted or unsubstituted polycyclic ring, L is a direct bond; a substituted or unsubstituted arylene; or a substituted or unsubstituted heteroarylene, R, R1, Ar1, and Ar2 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted hetero-cyclic group, or combine with an adjacent group to form a substituted or unsubstituted ring, a is an integer of 0 to 4, p is an integer of 0 to 5, and when a and p are each 2 or more, the structures in the parenthesis are the same as or different from each other.

Further, an exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

Advantageous Effects

The compound described in the present specification may be used as a material for an organic material layer of an organic light emitting device. The compound according to at least one exemplary embodiment may improve the efficiency, achieve low driving voltage and/or improve lifespan characteristics in the organic light emitting device. In particular, the compound described in the present specification may be used as a material for hole injection, hole transport, hole injection and hole transport, light emission, electron transport, or electron injection. In addition, the compound described in the present specification may be preferably used as a material for a light emitting layer, and electron transport or electron injection. Furthermore, more preferably, according to an exemplary embodiment of the present specification, the compound may be used as a material for a hole injection layer, a hole transporting layer, or an electron blocking layer.

DESCRIPTION OF DRAWINGS

FIG. 1 illustrates an example of an organic light emitting device composed of a substrate 1, a positive electrode 2, a light emitting layer 3, and a negative electrode 4.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4.

MODE FOR INVENTION

Hereinafter, the present specification will be described in more detail.

An exemplary embodiment of the present specification provides the compound represented by Chemical Formula 1.

Hereinafter, examples of the substituents will be described below, but are not limited thereto.

In the present specification,  or

means a moiety linked to another substituent.

In the present specification, the term "substituted or unsubstituted" means being unsubstituted or substituted with one or more substituents selected from the group consisting of deuterium; a halogen group; a nitrile group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; or a hetero-cyclic group, or being unsubstituted or substituted with a substituent to which two or more substituents are linked among the substituents exemplified above.

In the present specification, the "adjacent" group may mean a substituent substituted with an atom directly linked to an atom in which the corresponding substituent is substituted, a substituent disposed sterically closest to the corresponding substituent, or another substituent substituted with an atom in which the corresponding substituent is substituted. For example, two substituents substituted at the ortho position in a benzene ring and two substituents substituted with the same carbon in an aliphatic ring may be interpreted as groups which are "adjacent" to each other.

In the present specification, examples of a halogen group include fluorine, chlorine, bromine or iodine.

In the present specification, the number of carbon atoms of a carbonyl group is not particularly limited, but is preferably 1 to 40. Specifically, the carbonyl group may be a compound having the following structures, but is not limited thereto.

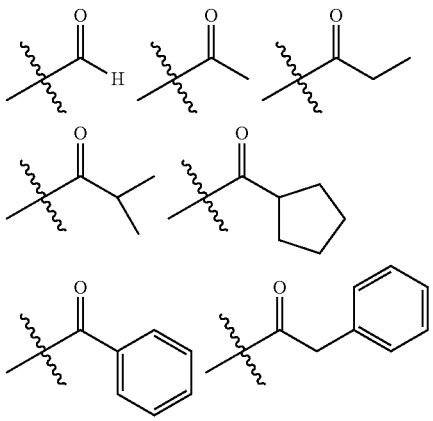

In the present specification, in an ester group, the oxygen of the ester group may be substituted with a straight-chained, branched, or cyclic alkyl group having 1 to 25 carbon atoms, or an aryl group having 6 to 25 carbon atoms. Specifically, the ester group may be a compound having the following structural formulae, but is not limited thereto.

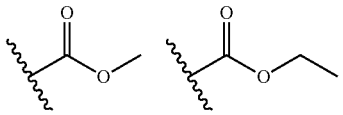

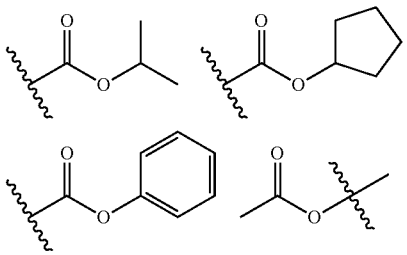

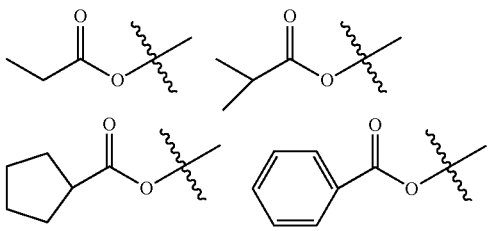

In the present specification, the number of carbon atoms of an imide group is not particularly limited, but is preferably 1 to 25. Specifically, the carbonyl group may be a compound having the following structures, but is not limited thereto.

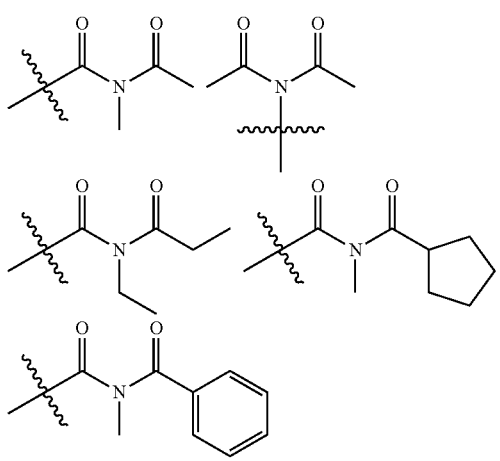

In the present specification, a silyl group may be represented by a chemical formula of —SiRR'R", and R, R', and R" may be each hydrogen; a substituted or unsubstituted alkyl group; or a substituted or unsubstituted aryl group. Specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, a boron group may be represented by a chemical formula of —BRR'R", and R, R', and R" may be each hydrogen; a substituted or unsubstituted alkyl group; or a substituted or unsubstituted aryl group. Specific examples of the boron group include a trimethylboron group, a triethylboron group, a t-butyldimethylboron group, a triphenylboron group, a phenylboron group, and the like, but are not limited thereto.

In the present specification, the alkyl group may be straight-chained or branched, and the number of carbon atoms thereof is not particularly limited, but is preferably 1 to 40. According to an exemplary embodiment, the number of carbon atoms of the alkyl group is 1 to 20. According to still another exemplary embodiment, the number of carbon atoms of the alkyl group is 1 to 10. According to yet another exemplary embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 4-methylhexyl, 5-methylhexyl, and the like, but are not limited thereto.

In the present specification, the alkenyl group may be straight-chained or branched, and the number of carbon atoms thereof is not particularly limited, but is preferably 2 to 40. According to an exemplary embodiment, the number of carbon atoms of the alkenyl group is 2 to 20. According to another exemplary embodiment, the number of carbon atoms of the alkenyl group is 2 to 10. According to still another exemplary embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

In the present specification, a cycloalkyl group is not particularly limited, but has preferably 3 to 60 carbon atoms, and according to an exemplary embodiment, the number of carbon atoms of the cycloalkyl group is 3 to 30. According to another exemplary embodiment, the number of carbon atoms of the cycloalkyl group is 3 to 20. According to another exemplary embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a polycyclic aryl group. The arylamine group including the two or more aryl groups may include a monocyclic aryl group, a polycyclic aryl group, or both a monocyclic aryl group and a polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroaryl group in the heteroarylamine group may be a monocyclic hetero-cyclic group or a polycyclic hetero-cyclic group. The heteroarylamine group including the two or more hetero-cyclic groups may include a monocyclic hetero-cyclic group, a polycyclic hetero-cyclic group, or both a monocyclic hetero-cyclic group and a polycyclic hetero-cyclic group.

In the present specification, the arylheteroarylamine group means an amine group substituted with an aryl group and a hetero-cyclic group.

In the present specification, examples of an arylphosphine group include a substituted or unsubstituted monoarylphosphine group, a substituted or unsubstituted diarylphosphine group, or a substituted or unsubstituted triarylphosphine group. The aryl group in the arylphosphine group may be a monocyclic aryl group, and may be a polycyclic aryl group. The arylphosphine group including the two or more aryl groups may include a monocyclic aryl group, a polycyclic aryl group, or both a monocyclic aryl group and a polycyclic aryl group.

In the present specification, an aryl group is not particularly limited, but has preferably 6 to 60 carbon atoms, and may be a monocyclic aryl group or a polycyclic aryl group. According to an exemplary embodiment, the number of carbon atoms of the aryl group is 6 to 30. According to an exemplary embodiment, the number of carbon atoms of the aryl group is 6 to 20. Examples of the monocyclic aryl group include a phenyl group, a biphenyl group, a terphenyl group, and the like, but are not limited thereto. Examples of the polycyclic aryl group include a naphthyl group, an anthracenyl group, a phenanthryl group, a pyrenyl group, a perylenyl group, a chrysenyl group, a fluorenyl group, a fluoranthene group, a triphenylene group, and the like, but are not limited thereto.

In the present specification, a fluorenyl group may be substituted, and two substituents may combine with each other to form a spiro structure.

When the fluorenyl group is substituted, the fluorenyl group may be

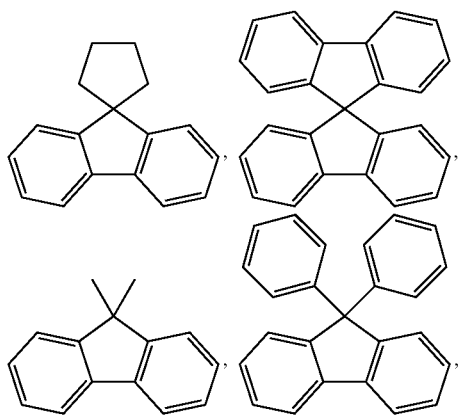

and the like. However, the fluorenyl group is not limited thereto.

In the present specification, the hetero-cyclic group is a hetero-cyclic group including one or more of N, O, P, S, Si, and Se as a hetero atom, and the number of carbon atoms thereof is not particularly limited, but is preferably 2 to 60. Examples of the hetero-cyclic group include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a qinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the description on the above-described hetero-cyclic group may be applied to a heteroaryl group except for an aromatic group.

In the present specification, the description on the above-described aryl group may be applied to an aryl group of an aryloxy group, an arylthioxy group, an arylsulfoxy group, an arylphosphine group, an aralkyl group, an aralkylamine group, an aralkenyl group, an alkylaryl group, an arylamine group, and an arylheteroarylamine group.

In the present specification, the description on the above-described alkyl group may be applied to an alkyl group of an alkylthioxy group, an alkylsulfoxy group, an aralkyl group, an aralkylamine group, an alkylaryl group, and an alkylamine group.

In the present specification, the description on the above-described hetero-cyclic group may be applied to a heteroaryl group of a heteroaryl group, a heteroarylamine group, and an arylheteroarylamine group.

In the present specification, the description on the above-described alkenyl group may be applied to an alkenyl group of an aralkenyl group.

In the present specification, the description on the above-described aryl group may be applied to an arylene except for a divalent arylene group.

In the present specification, the description on the above-described hetero-cyclic group may be applied to a heteroarylene except for a divalent heteroarylene group.

In the present specification, the polycyclic ring means two or more cyclic rings, and the ring means forming a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a condensed ring thereof.

In the present specification, the meaning of combining with an adjacent group to form a ring means combining with an adjacent group to form a substituted or unsubstituted aliphatic hydrocarbon ring; a substituted or unsubstituted aromatic hydrocarbon ring; a substituted or unsubstituted aliphatic hetero ring; a substituted or unsubstituted aromatic hetero ring; or a condensed ring thereof.

In the present specification, the aliphatic hydrocarbon ring means a ring composed only of carbon and hydrogen atoms as a ring which is not an aromatic group.

In the present specification, examples of the aromatic hydrocarbon ring include a phenyl group, a naphthyl group, an anthracenyl group, and the like, but are not limited thereto.

In the present specification, the aliphatic hetero ring means an aliphatic ring including one or more of hetero atoms.

In the present specification, the aromatic hetero ring means an aromatic ring including one or more of hetero atoms.

In the present specification, the aliphatic hydrocarbon ring, the aromatic hydrocarbon ring, the aliphatic hetero ring, and the aromatic hetero ring may be monocyclic or polycyclic.

According to an exemplary embodiment of the present specification, Chemical Formula 1 may be represented by any one of the following Chemical Formulae 2 to 4.

[Chemical Formula 2]

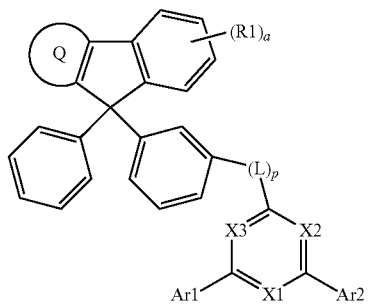

[Chemical Formula 3]

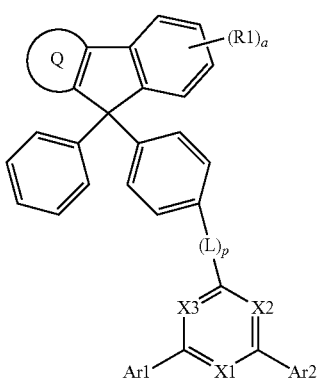

[Chemical Formula 4]

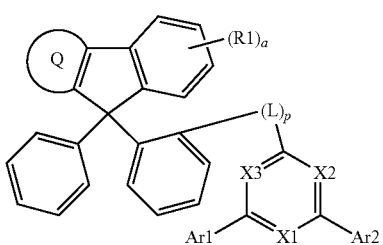

In Chemical Formulae 2 to 4, the definitions of Q, R1, L, X1 to X3, Ar1, Ar2, a, and p are the same as those defined in Chemical Formula 1.

According to an exemplary embodiment of the present specification, Chemical Formula 1 may be represented by the following Chemical Formula 5.

[Chemical Formula 5]

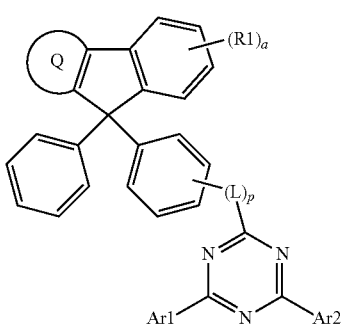

In Chemical Formula 5, the definitions of Q, R1, L, Ar1, Ar2, a, and p are the same as those defined in Chemical Formula 1.

According to an exemplary embodiment of the present specification, Q is a substituted or unsubstituted aliphatic polycyclic hydrocarbon ring; a substituted or unsubstituted aromatic polycyclic hydrocarbon ring; a substituted or unsubstituted aliphatic polycyclic hetero ring; a substituted or unsubstituted aromatic polycyclic hetero ring; or a condensed ring thereof.

According to an exemplary embodiment of the present specification, Q is a substituted or unsubstituted monocyclic to tetracyclic ring.

According to an exemplary embodiment of the present specification, Q is a substituted or unsubstituted aromatic polycyclic hydrocarbon ring; or a substituted or unsubstituted aromatic polycyclic hetero ring.

According to an exemplary embodiment of the present specification, Q is a substituted or unsubstituted naphthyl group; a substituted or unsubstituted anthracenyl group; a substituted or unsubstituted phenanthryl group; a substituted or unsubstituted pyrenyl group; a substituted or unsubstituted perylenyl group; a substituted or unsubstituted chrysenyl group; a substituted or unsubstituted fluorenyl group; a substituted or unsubstituted fluoranthene group; a substituted or unsubstituted triphenylene group; a substituted or unsubstituted quinolinyl group; a substituted or unsubstituted quinazoline group; a substituted or unsubstituted quinoxalinyl group; a substituted or unsubstituted phthalazinyl group; a substituted or unsubstituted pyridopyrimidinyl group; a substituted or unsubstituted pyridopyrazinyl group; a substituted or unsubstituted pyrazinopyrazinyl group; a substituted or unsubstituted isoquinoline group; a substituted or unsubstituted indole group; a substituted or unsubstituted carbazole group; a substituted or unsubstituted benzoxazole group; a substituted or unsubstituted benzimidazole group; a substituted or unsubstituted benzothiazole group; a substituted or unsubstituted benzocarbazole group; a substituted or unsubstituted benzothiophene group; a substituted or unsubstituted dibenzothiophene group; a substituted or unsubstituted benzofuranyl group; a substituted or unsubstituted phenanthroline group; a substituted or unsubstituted thiazolyl group; a substituted or unsubstituted isoxazolyl group; a substituted or unsubstituted oxadiazolyl group; a substituted or unsubstituted thiadiazolyl group; a substituted or unsubstituted benzothiazolyl group; a substituted or unsubstituted phenothiazinyl group; or a substituted or unsubstituted dibenzofuranyl group.

According to an exemplary embodiment of the present specification, Q is a substituted or unsubstituted naphthyl group; a substituted or unsubstituted anthracenyl group; a substituted or unsubstituted pyrenyl group; a substituted or unsubstituted chrysenyl group; a substituted or unsubstituted fluoranthene group; a substituted or unsubstituted triphenylene group; a substituted or unsubstituted dibenzothiophene group; or a substituted or unsubstituted dibenzofuranyl group.

According to an exemplary embodiment of the present specification, Q is a substituted or unsubstituted aromatic polycyclic hydrocarbon ring.

According to an exemplary embodiment of the present specification, Q is a substituted or unsubstituted naphthyl group; a substituted or unsubstituted anthracenyl group; a substituted or unsubstituted phenanthryl group; a substituted or unsubstituted pyrenyl group; a substituted or unsubstituted perylenyl group; a substituted or unsubstituted chrysenyl group; a substituted or unsubstituted fluorenyl group; a substituted or unsubstituted fluoranthene group; or a substituted or unsubstituted triphenylene group.

According to an exemplary embodiment of the present specification, Q is a substituted or unsubstituted naphthyl group; a substituted or unsubstituted anthracenyl group; a substituted or unsubstituted pyrenyl group; a substituted or unsubstituted fluoranthene group; or a substituted or unsubstituted triphenylene group.

According to an exemplary embodiment of the present specification, Q is a naphthyl group; an anthracenyl group; a pyrenyl group; a fluoranthene group; or a triphenylene group.

According to an exemplary embodiment of the present specification, Q is a substituted or unsubstituted naphthyl group.

According to an exemplary embodiment of the present specification, Chemical Formula 1 may be represented by any one of the following Chemical Formulae 6 to 11.

[Chemical Formula 6]

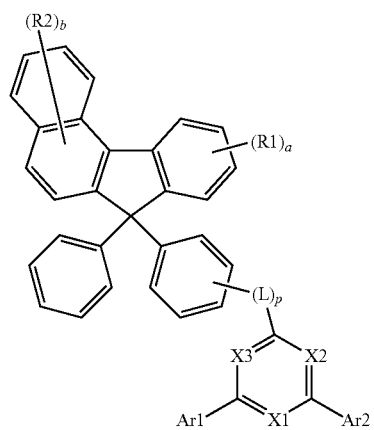

[Chemical Formula 7]

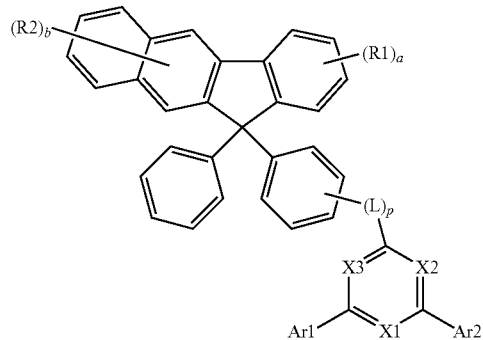

[Chemical Formula 8]

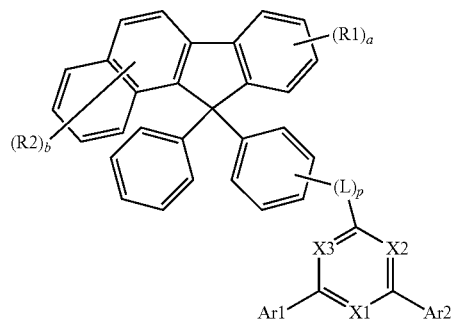

[Chemical Formula 9]

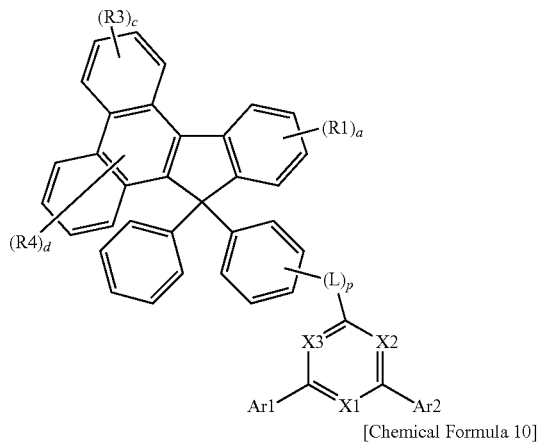

[Chemical Formula 10]

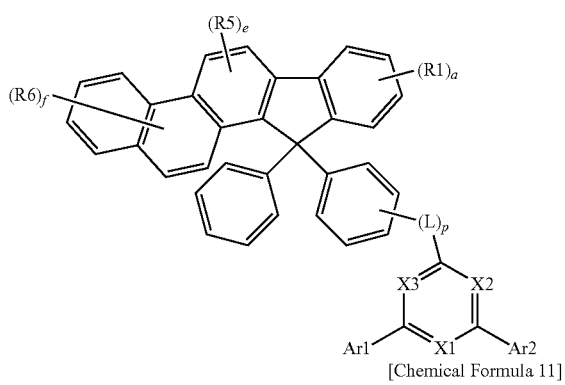

[Chemical Formula 11]

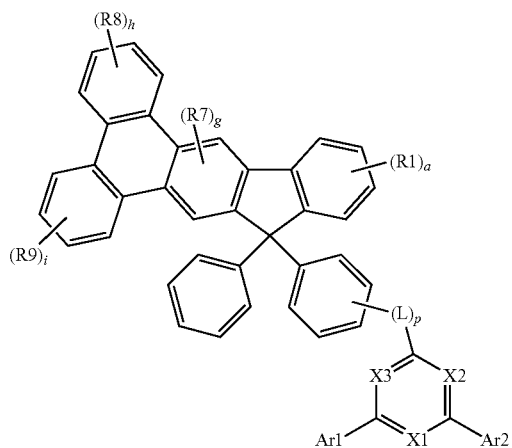

In Chemical Formulae 6 to 11, the definitions of R1, L, X1 to X3, Ar1, Ar2, a, and p are the same as those defined in Chemical Formula 1, R2 to R9 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted hetero-cyclic group, or combine with an adjacent group to form a substituted or unsubstituted ring, b and f are the same as or different from each other, and are each independently an integer of 0 to 6, c, d, h, and i are the same as or different from each other, and are each independently an integer of 0 to 4, e and g are the same as or different from each other, and are each independently an integer of 0 to 2, and when b, c, d, e, f, g, h, and i are each 2 or more, the structures in the parenthesis are the same as or different from each other.

According to an exemplary embodiment of the present specification, Q is a substituted or unsubstituted aromatic polycyclic hetero ring.

According to an exemplary embodiment of the present specification, Chemical Formula 1 may be represented by the following Chemical Formula 12.

[Chemical Formula 12]

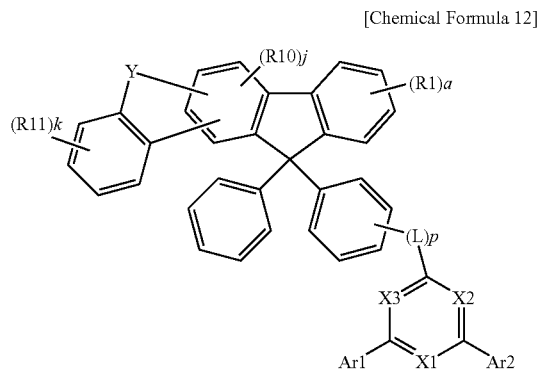

In Chemical Formula 12, the definitions of R1, L, X1 to X3, Ar1, Ar2, a, and p are the same as those defined in Chemical Formula 1, Y is S, O, or NR, R, R10, and R11 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted hetero-cyclic group, or combine with an adjacent group to form a substituted or unsubstituted ring, j is an integer of 0 to 2, k is an integer of 0 to 4, and when j and k are each 2 or more, the structures in the parenthesis are the same as or different from each other.

According to an exemplary embodiment of the present specification, Chemical Formula 1 may be represented by any one of the following Chemical Formulae 13 to 15.

[Chemical Formula 13]

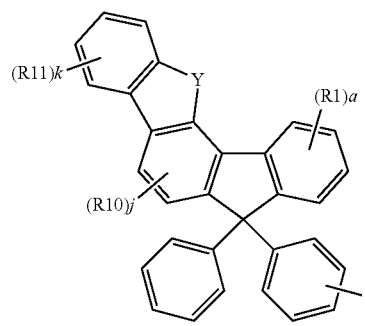

[Chemical Formula 14]

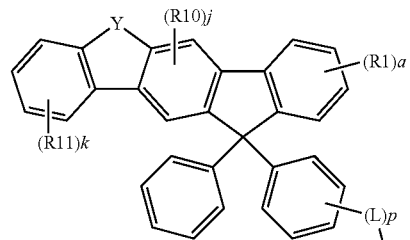

[Chemical Formula 15]

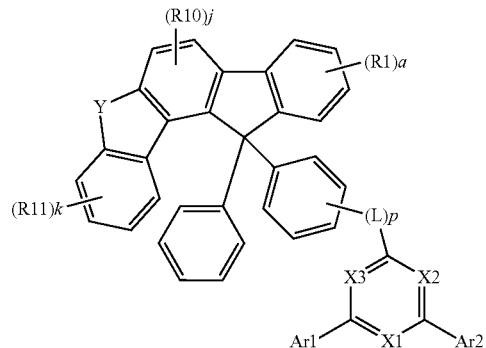

In Chemical Formulae 13 to 15, the definitions of R1, L, X1 to X3, Ar1, Ar2, a, and p are the same as those defined in Chemical Formula 1, Y is S, O, or NR, R, R10, and R11 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted hetero-cyclic group, or combine with an adjacent group to form a substituted or unsubstituted ring, j is an integer of 0 to 2, k is an integer of 0 to 4, and when j and k are each 2 or more, the structures in the parenthesis are the same as or different from each other.

According to an exemplary embodiment of the present specification, Chemical Formula 1 may be represented by any one of the following Chemical Formulae 16 to 18.

[Chemical Formula 16]

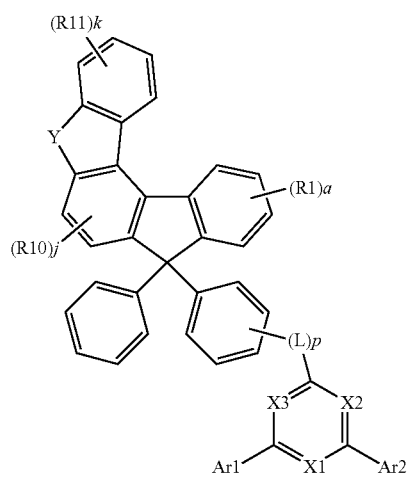

[Chemical Formula 17]

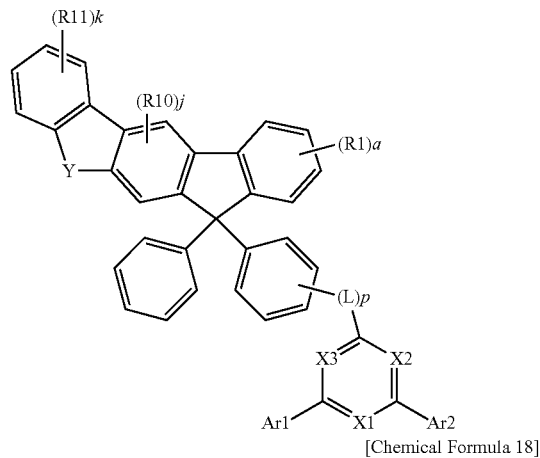

[Chemical Formula 18]

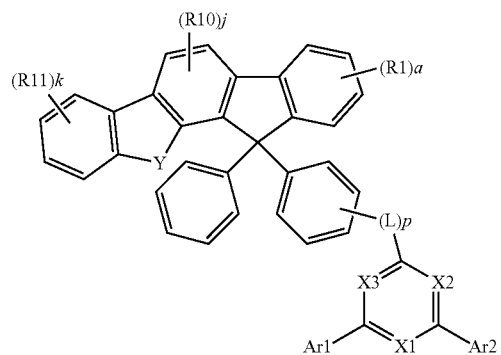

In Chemical Formulae 16 to 18, the definitions of R1, L, X1 to X3, Ar1, Ar2, a, and p are the same as those defined in Chemical Formula 1, Y is S, O, or NR, R, R10, and R11 are the same as or different from each other, and are each independently hydrogen; deuterium; a halogen group; a nitrile group; a nitro group; a hydroxy group; a carbonyl group; an ester group; an imide group; an amino group; a substituted or unsubstituted silyl group; a substituted or unsubstituted boron group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted aralkyl group; a substituted or unsubstituted aralkenyl group; a substituted or unsubstituted alkylaryl group; a substituted or unsubstituted alkylamine group; a substituted or unsubstituted aralkylamine group; a substituted or unsubstituted heteroarylamine group; a substituted or unsubstituted arylamine group; a substituted or unsubstituted arylheteroarylamine group; a substituted or unsubstituted arylphosphine group; a substituted or unsubstituted phosphine oxide group; a substituted or unsubstituted aryl group; or a substituted or unsubstituted hetero-cyclic group, or combine with an adjacent group to form a substituted or unsubstituted ring, j is an integer of 0 to 2, k is an integer of 0 to 4, and when j and k are each 2 or more, the structures in the parenthesis are the same as or different from each other.

According to an exemplary embodiment of the present specification, L is a direct bond; or a substituted or unsubstituted arylene.

According to an exemplary embodiment of the present specification, L is a direct bond; or an arylene which is unsubstituted or substituted with one or more substituents selected from the group consisting of deuterium, a halogen group, an amino group, a nitrile group, a nitro group, an alkyl group, an alkenyl group, an alkoxy group, a cycloalkyl group, an aryl group, and a hetero-cyclic group.

According to an exemplary embodiment of the present specification, L is a direct bond; or an arylene which is unsubstituted or substituted with one or more substituents selected from the group consisting of deuterium, a halogen group, an alkyl group, an aryl group, and a hetero-cyclic group.

According to an exemplary embodiment of the present specification, L is a direct bond; or an arylene having 6 to 40 carbon atoms.

According to an exemplary embodiment of the present specification, L is a direct bond; or arylene.

According to an exemplary embodiment of the present specification, L is a direct bond.

According to an exemplary embodiment of the present specification, L is a substituted or unsubstituted arylene having 6 to 30 carbon atoms.

According to an exemplary embodiment of the present specification, L is a substituted or unsubstituted phenyl group, a substituted or unsubstituted biphenyl group, a substituted or unsubstituted terphenyl group, or a substituted or unsubstituted naphthyl group.

According to an exemplary embodiment of the present specification, L is a phenyl group.

According to an exemplary embodiment of the present specification, L is a naphthyl group.

According to an exemplary embodiment of the present specification, Ar1 and Ar2 are the same as or different from each other, and are each independently a substituted or unsubstituted aryl group; or a substituted or unsubstituted hetero-cyclic group.

According to an exemplary embodiment of the present specification, Ar1 and Ar2 are the same as or different from each other, and are each independently an aryl group; or a hetero-cyclic group.

According to an exemplary embodiment of the present specification, Ar1 and Ar2 are the same as or different from each other, and are each independently an aryl group.

According to an exemplary embodiment of the present specification, Ar1 and Ar2 are the same as or different from each other, and are each independently an aryl group having 6 to 30 carbon atoms.

According to an exemplary embodiment of the present specification, Ar1 and Ar2 are the same as or different from each other, and are each independently a hetero-cyclic group.

According to an exemplary embodiment of the present specification, Ar1 and Ar2 are the same as or different from each other, and are each independently a hetero-cyclic group having 3 to 40 carbon atoms.

According to an exemplary embodiment of the present specification, Ar1 and Ar2 are the same as or different from each other, and are each independently hydrogen, an alkyl group, an aryl group, or a hetero-cyclic group.

According to an exemplary embodiment of the present specification, Ar1 and Ar2 are the same as or different from each other, and are each independently a substituted or unsubstituted aryl group.

According to an exemplary embodiment of the present specification, Ar1 and Ar2 are the same as or different from each other, and are each independently a substituted or unsubstituted phenyl group; a substituted or unsubstituted biphenyl group; or a substituted or unsubstituted naphthyl group.

According to an exemplary embodiment of the present specification, Ar1 and Ar2 are the same as or different from each other, and are each independently a phenyl group; a biphenyl group; or a naphthyl group.

According to an exemplary embodiment of the present specification, Ar1 and Ar2 are a substituted or unsubstituted phenyl group.

According to an exemplary embodiment of the present specification, Ar1 and Ar2 are a phenyl group.

According to an exemplary embodiment of the present specification, Ar1 and Ar2 are the same as or different from each other, and are each independently a substituted or unsubstituted carbazole group, a substituted or unsubstituted dibenzofuran group, or a substituted or unsubstituted dibenzothiophene group.

According to an exemplary embodiment of the present specification, Ar1 and Ar2 are the same as or different from each other, and are each independently a carbazole group which is unsubstituted or substituted with a phenyl group.

According to an exemplary embodiment of the present specification, Ar1 and Ar2 are the same as or different from each other, and are each independently a carbazole group.

According to an exemplary embodiment of the present specification, Ar1 and Ar2 are the same as or different from each other, and are each independently a dibenzothiophene group which is unsubstituted or substituted with a phenyl group.

According to an exemplary embodiment of the present specification, Ar1 and Ar2 are the same as or different from each other, and are each independently a dibenzothiophene group.

According to an exemplary embodiment of the present specification, Ar1 and Ar2 are the same as or different from each other, and are each independently a dibenzofuran group which is unsubstituted or substituted with a phenyl group.

According to an exemplary embodiment of the present specification, Ar1 and Ar2 are the same as or different from each other, and are each independently a dibenzofuran group.

According to an exemplary embodiment of the present specification, R1 is hydrogen; deuterium; a substituted or unsubstituted alkyl group; a substituted or unsubstituted aryl group; or a substituted or unsubstituted hetero-cyclic group.

According to an exemplary embodiment of the present specification, R1 is hydrogen; deuterium; an alkyl group; an aryl group; or a hetero-cyclic group.

According to an exemplary embodiment of the present specification, R1 is hydrogen.

According to an exemplary embodiment of the present specification, at least one of X1 to X3 is N.

According to an exemplary embodiment of the present specification, X1 is N.

According to an exemplary embodiment of the present specification, X2 is N.

According to an exemplary embodiment of the present specification, X3 is N.

According to an exemplary embodiment of the present specification, X1 to X3 are each N.
According to an exemplary embodiment of the present specification, Chemical Formula 1 may be any one selected from the following compounds.
Compound 1
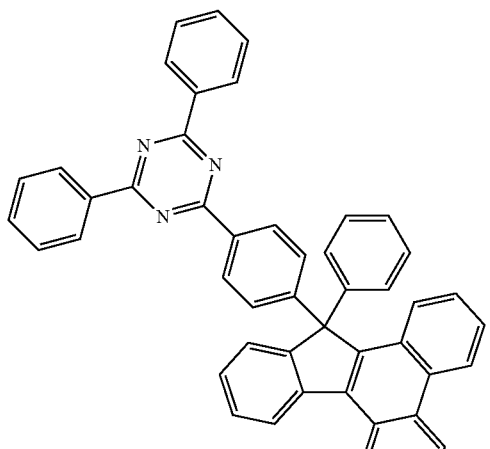
Compound 2
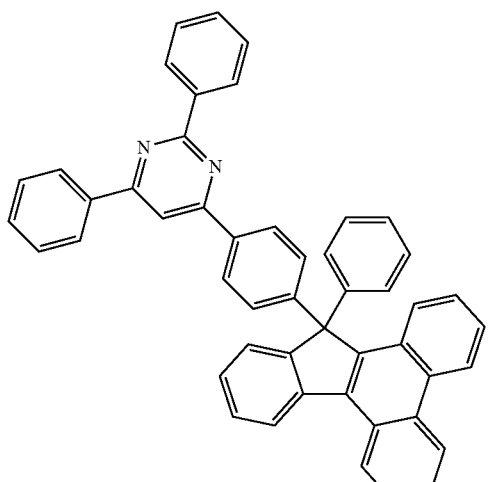
Compound 3
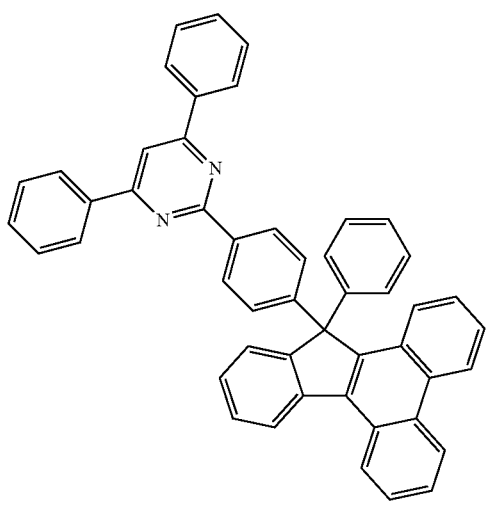
Compound 4
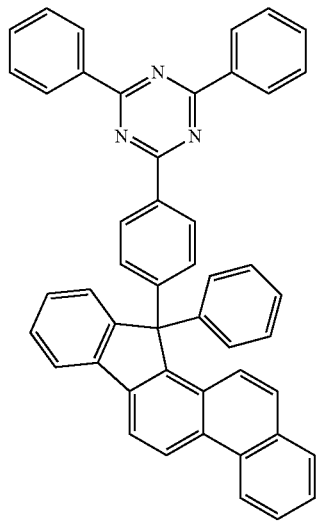
Compound 5
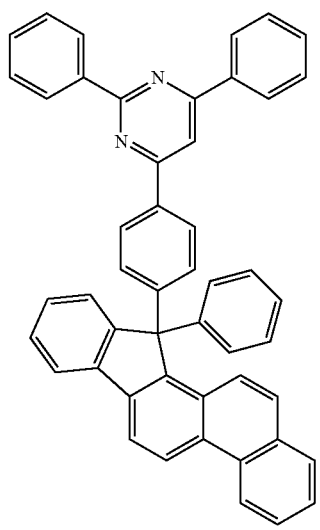
Compound 6
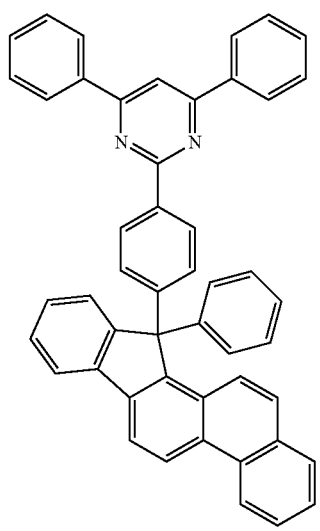

Compound 7
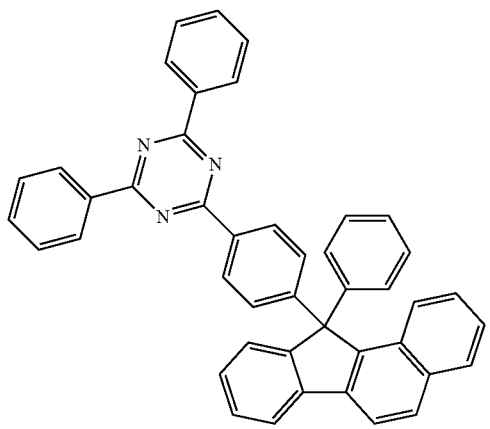
Compound 8
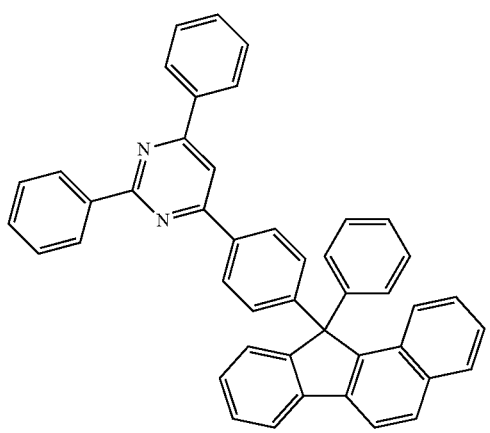
Compound 9
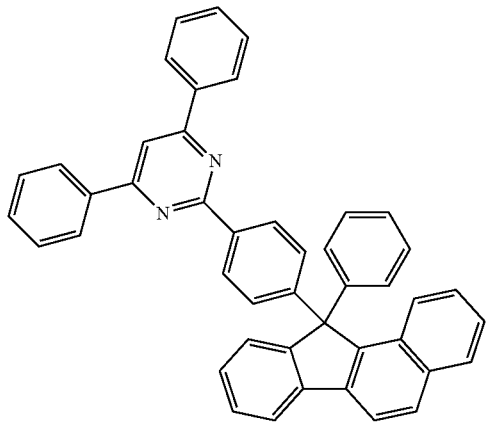
Compound 10
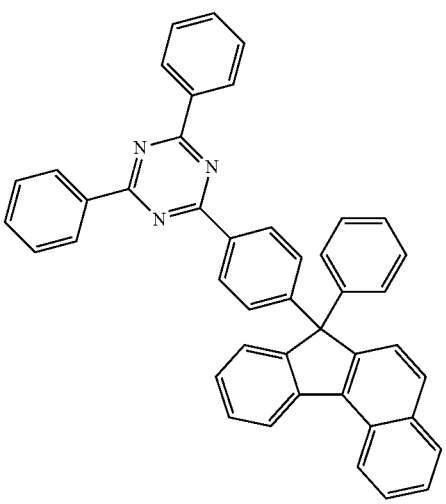
Compound 11
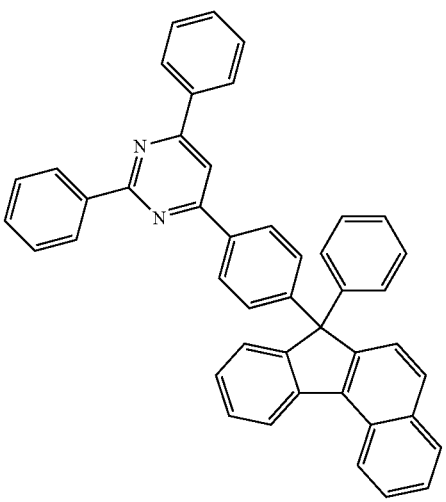
Compound 12
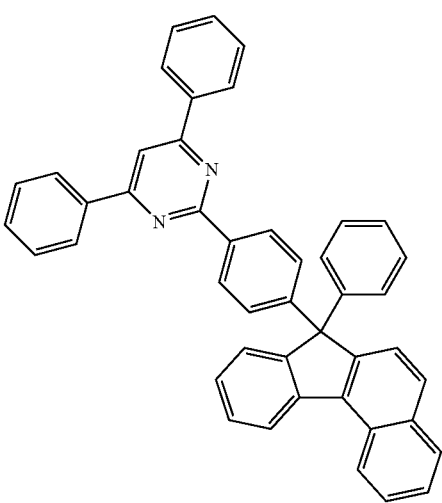

Compound 13
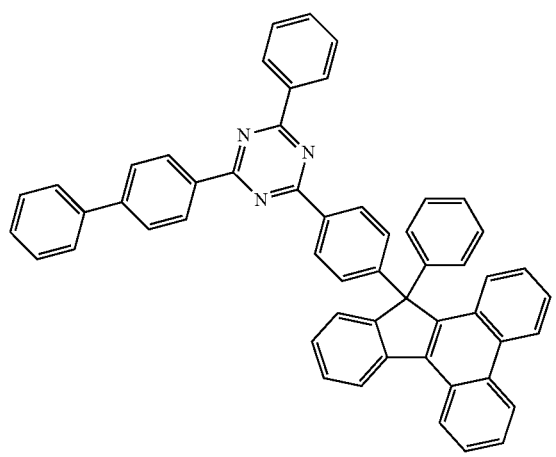
Compound 14
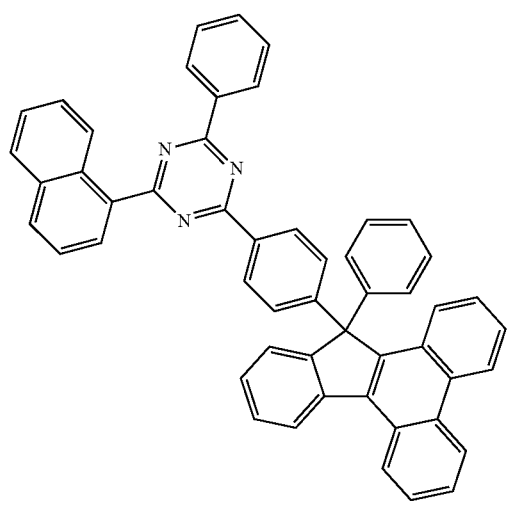
Compound 15
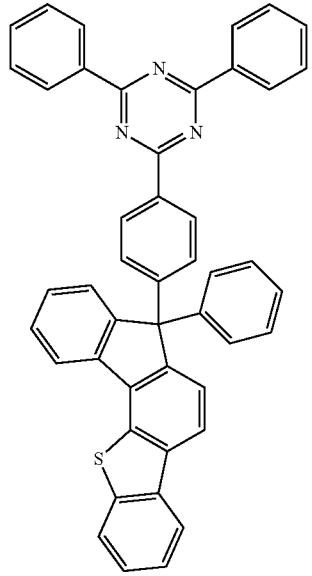
Compound 16
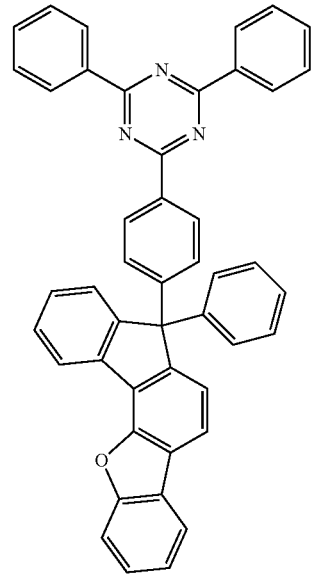
Compound 17
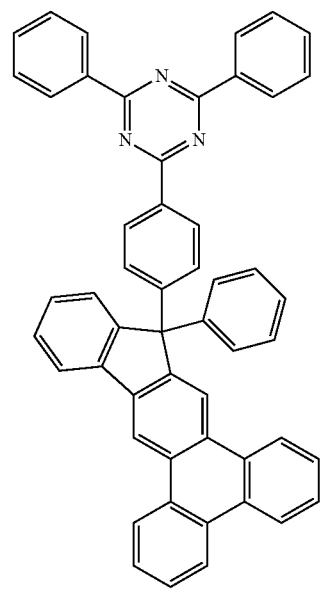
Compound 18
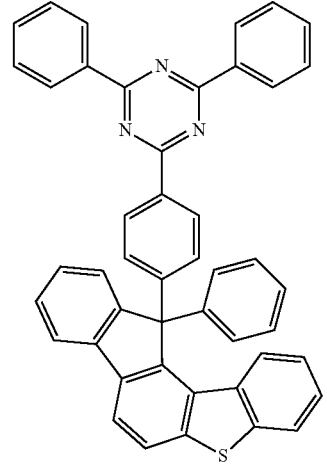

Compound 19
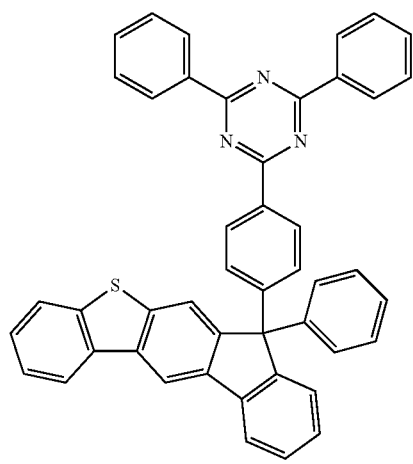
Compound 20
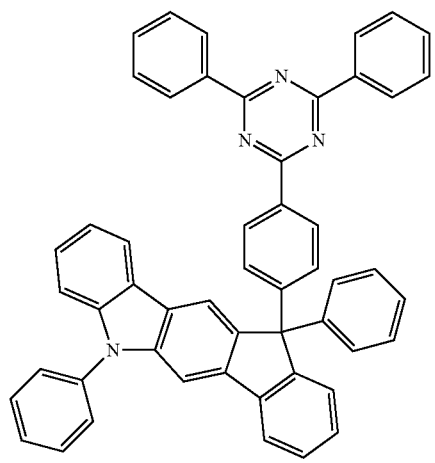
Compound 21
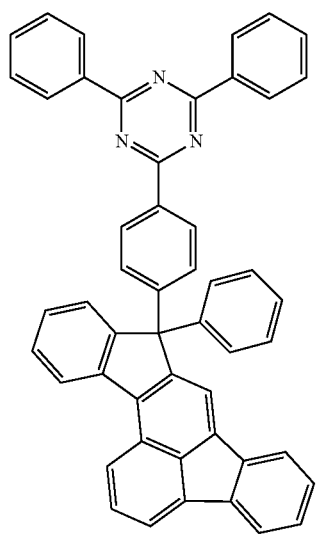
Compound 22
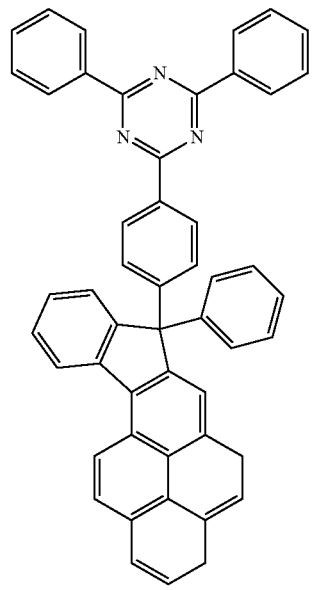
Compound 23
Compound 24
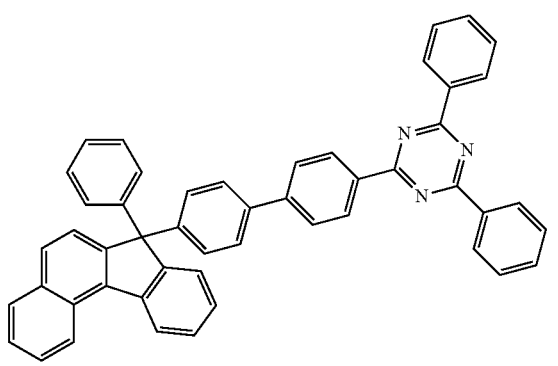

Compound 25
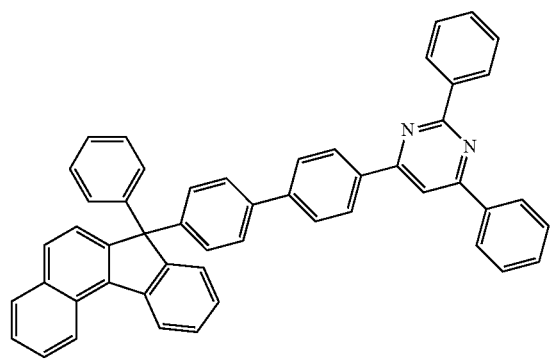
Compound 26
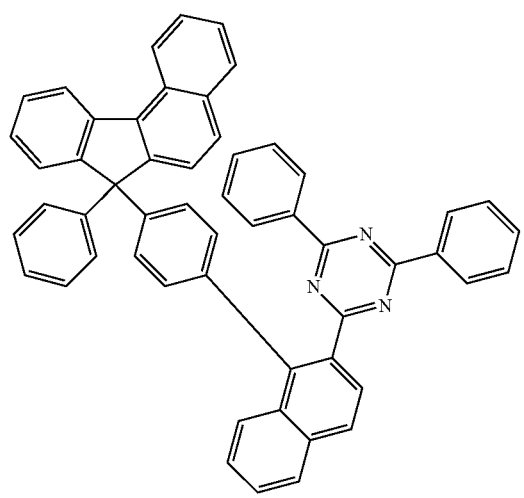
Compound 27
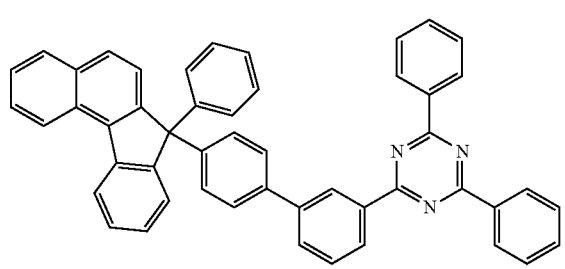
Compound 28
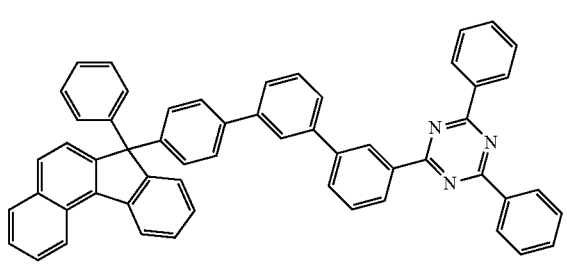
Compound 29
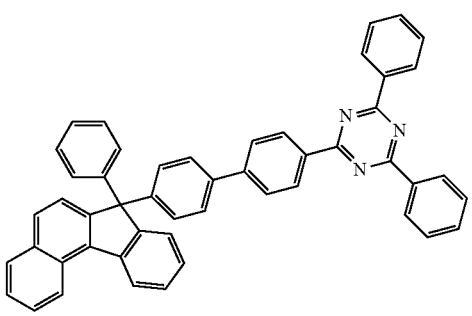
Compound 30
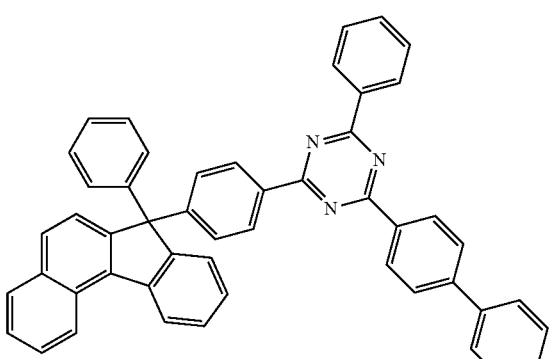
Compound 31
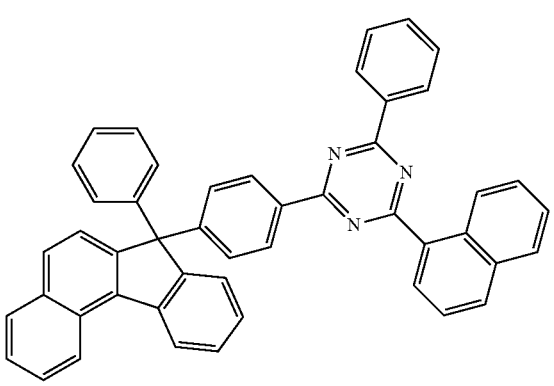
Compound 32
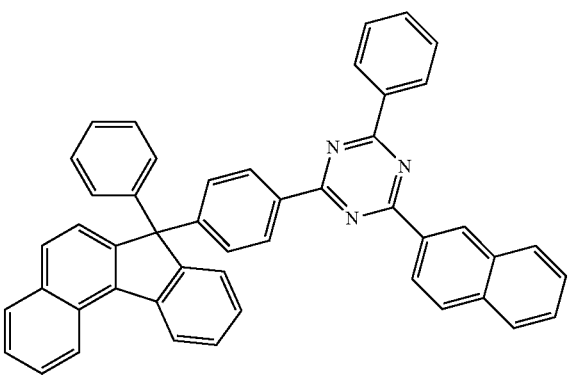

Compound 33
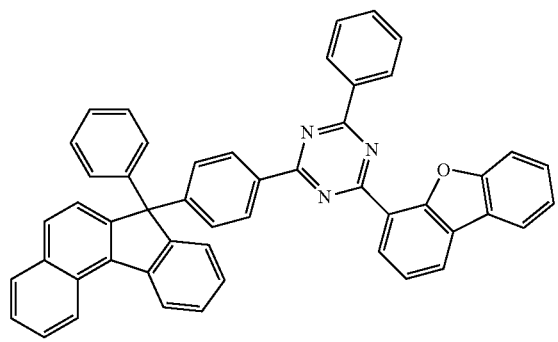

Compound 34
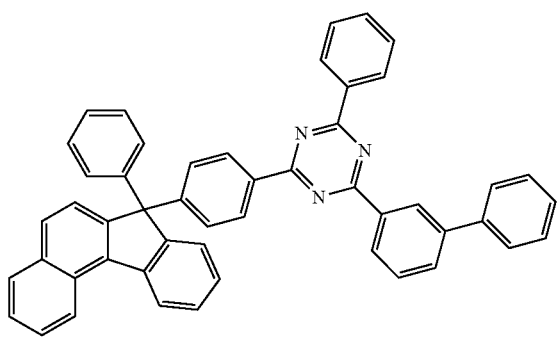

Compound 35

Compound 36
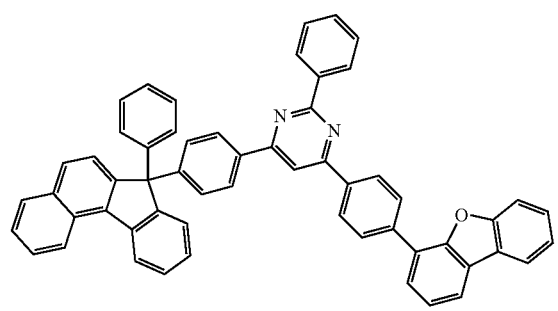

Compound 37
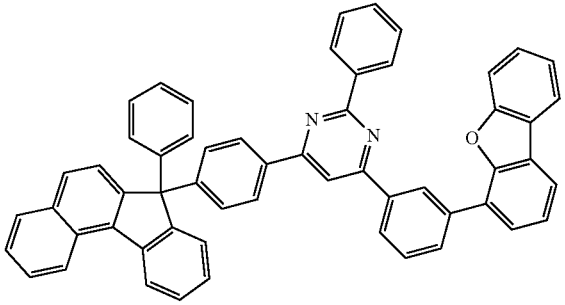

Compound 38

Compound 39
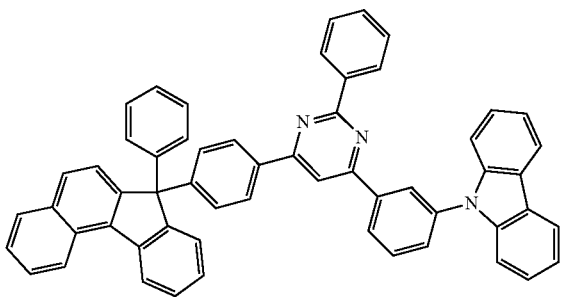

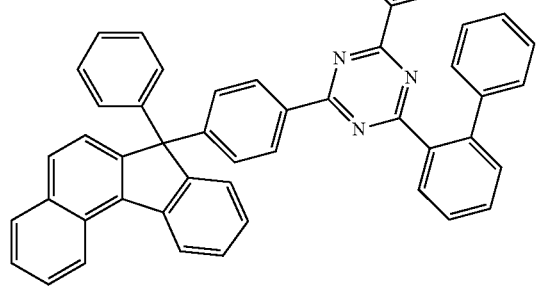

Further, the present specification provides an organic light emitting device including the compound represented by Chemical Formula 1.

An exemplary embodiment of the present specification provides an organic light emitting device including: a first electrode; a second electrode provided to face the first electrode; and one or more organic material layers provided between the first electrode and the second electrode, in which one or more layers of the organic material layers include the compound of Chemical Formula 1.

The organic material layer of the organic light emitting device of the present specification may also be composed of a single-layered structure, but may be composed of a multi-layered structure in which two or more organic material layers are stacked. For example, the organic light emitting device of the present invention may have a structure including a hole injection layer, a hole transporting layer, a light emitting layer, an electron transporting layer, an electron injection layer, and the like as organic material layers. However, the structure of the organic light emitting device is not limited thereto, and may include a fewer number of organic layers.

It is possible to include a structure of the following Chemical Formula 1-A as a material for a dopant of the light emitting layer of the organic material layers of the organic light emitting device of the present specification.

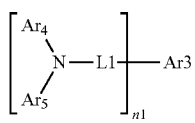

[Chemical Formula 1-A]

In Chemical Formula 1-A,

Ar3 is a substituted or unsubstituted benzofluorene group; a substituted or unsubstituted fluoranthene group; a substituted or unsubstituted pyrene group; or a substituted or unsubstituted chrysene group, L1 is a direct bond or a substituted or unsubstituted arylene group; or a substituted or unsubstituted heteroarylene group, Ar4 and Ar5 are the same as or different from each other, and are a substituted or unsubstituted aryl group; a substituted or unsubstituted silyl group; a substituted or unsubstituted alkyl group; a substituted or unsubstituted aralalkyl group; or a substituted or unsubstituted hetero-cyclic group, Ar4 and Ar5 may combine with each other to form a ring, n1 is an integer of 1 or more, and when n1 is 2 or more, the structures in the parenthesis are the same as or different from each other.

In an exemplary embodiment of the present specification, Ar3 is a pyrene group which is unsubstituted or substituted with hydrogen, deuterium, a methyl group, an ethyl group, or a tert-butyl group.

In an exemplary embodiment of the present specification, Ar3 is a pyrene group.

In an exemplary embodiment of the present specification, Ar4 and Ar5 are the same as or different from each other, and are a substituted or unsubstituted aryl group having 6 to 30 carbon atoms.

In an exemplary embodiment of the present specification, Ar4 and Ar5 are the same as or different from each other, and are an aryl group which is unsubstituted or substituted with a methyl group, an ethyl group, a tert-butyl group, a cyano group, or a silyl group.

In an exemplary embodiment of the present specification, Ar4 and Ar5 are the same as or different from each other, and are a substituted or unsubstituted phenyl group, a substituted or unsubstituted biphenyl group, or a substituted or unsubstituted terphenyl group.

In an exemplary embodiment of the present specification, Ar4 and Ar5 are the same as or different from each other, and are a phenyl group which is unsubstituted or substituted with a methyl group, an ethyl group, a tert-butyl group, a cyano group, or a silyl group.

In an exemplary embodiment of the present specification, Ar4 and Ar5 are the same as or different from each other, and are a biphenyl group which is unsubstituted or substituted with a methyl group, an ethyl group, a tert-butyl group, a cyano group, or a silyl group.

In an exemplary embodiment of the present specification, Ar4 and Ar5 are the same as or different from each other, and are a terphenyl group which is unsubstituted or substituted with a methyl group, an ethyl group, a tert-butyl group, a cyano group, or a silyl group.

In an exemplary embodiment of the present specification, Ar4 and Ar5 are the same as or different from each other, and are a substituted or unsubstituted hetero-cyclic group having 6 to 30 carbon atoms.

In an exemplary embodiment of the present specification, Ar4 and Ar5 are the same as or different from each other, and are a hetero-cyclic group which is unsubstituted or substituted with a methyl group, an ethyl group, a tert-butyl group, a cyano group, a silyl group, or a phenyl group.

In an exemplary embodiment of the present specification, Ar4 and Ar5 are the same as or different from each other, and are a dibenzofuran group which is unsubstituted or substituted with a methyl group, an ethyl group, a tert-butyl group, a cyano group, a silyl group, or a phenyl group.

In an exemplary embodiment of the present specification, the organic material layer includes a hole injection layer, a hole transporting layer, or a layer which simultaneously injects and transports holes, and the hole injection layer, the hole transporting layer, or the layer which simultaneously injects and transports holes includes the compound of Chemical Formula 1.

In another exemplary embodiment, the organic material layer includes a light emitting layer, and the light emitting layer includes the compound of Chemical Formula 1.

In an exemplary embodiment of the present specification, the organic material layer includes an electron transporting layer or an electron injection layer, and the electron transporting layer or the electron injection layer includes the compound of Chemical Formula 1.

In an exemplary embodiment of the present specification, the electron transporting layer, the electron injection layer, or the layer which simultaneously transports and injects electrons includes the compound of Chemical Formula 1.

In another exemplary embodiment, the organic material layer includes a light emitting layer and an electron transporting layer, and the electron transporting layer includes the compound of Chemical Formula 1.

In still another exemplary embodiment, the organic light emitting device may be an organic light emitting device having a structure (normal type) in which a positive electrode, one or more organic material layers, and a negative electrode are sequentially stacked on a substrate.

In yet another exemplary embodiment, the organic light emitting device may be an organic light emitting device having a reverse-direction structure (inverted type) in which a negative electrode, one or more organic material layers, and a positive electrode are sequentially stacked on a substrate.

For example, the structure of the organic light emitting device according to an exemplary embodiment of the present specification is illustrated in FIGS. 1 and 2.

FIG. 1 illustrates an example of an organic light emitting device composed of a substrate 1, a positive electrode 2, a light emitting layer 3, and a negative electrode 4. In the structure, the compound may be included in the light emitting layer.

FIG. 2 illustrates an example of an organic light emitting device composed of a substrate 1, a positive electrode 2, a hole injection layer 5, a hole transporting layer 6, a light emitting layer 7, an electron transporting layer 8, and a negative electrode 4. In the structure, the compound may be included in one or more layers of the hole injection layer, the hole transporting layer, the light emitting layer, and the electron transporting layer.

The organic light emitting device of the present specification may be manufactured by the materials and methods known in the art, except that one or more layers of the organic material layers include the compound of the present specification, that is, the compound of Chemical Formula 1.

When the organic light emitting device includes a plurality of organic material layers, the organic material layers may be formed of the same material or different materials.

An exemplary embodiment of the present specification provides an organic light emitting device including: a first electrode; a second electrode provided to face the first electrode; a light emitting layer provided between the first electrode and the second electrode; and two or more organic material layers provided between the light emitting layer and the first electrode, or between the light emitting layer and the second electrode, in which at least one of the two or more organic material layers includes the hetero-cyclic compound. In one exemplary embodiment, as the two or more organic material layers, two or more may be selected from the group consisting of an electron transporting layer, an electron injection layer, a layer which simultaneously transports and injects electrons, and a hole blocking layer.

In an exemplary embodiment of the present specification, the organic material layer includes two or more electron transporting layers, and at least one of the two or more electron transporting layers includes the hetero-cyclic compound. Specifically, in an exemplary embodiment of the present specification, the hetero-cyclic compound may also be included in one layer of the two or more electron transporting layers, and may be included in each of the two or more electron transporting layers.

In addition, in an exemplary embodiment of the present specification, when the hetero-cyclic compound is included in each of the two or more electron transporting layers, the other materials except for the hetero-cyclic compound may be the same as or different from each other.

The organic light emitting device of the present specification may be manufactured by the materials and methods known in the art, except that one or more layers of the organic material layers include the compound of Chemical Formula 1, that is, the compound represented by Chemical Formula 1.

For example, the organic light emitting device of the present specification may be manufactured by sequentially stacking a first electrode, an organic material layer, and a second electrode on a substrate. In this case, the organic light emitting device may be manufactured by depositing a metal or a metal oxide having conductivity, or an alloy thereof on a substrate to form a positive electrode, forming an organic material layer including a hole injection layer, a hole transporting layer, a light emitting layer, and an electron transporting layer thereon, and then depositing a material, which may be used as a negative electrode, thereon, by using a physical vapor deposition (PVD) method such as sputtering or e-beam evaporation. In addition to the method as described above, an organic light emitting device may be made by sequentially depositing a negative electrode material, an organic material layer, and a positive electrode material on a substrate.

Further, the compound of Chemical Formula 1 may be formed as an organic material layer by not only a vacuum deposition method, but also a solution application method when an organic light emitting device is manufactured. Here, the solution application method means spin coating, dip coating, doctor blading, inkjet printing, screen printing, a spray method, roll coating, and the like, but is not limited thereto.

In addition to the method as described above, an organic light emitting device may also be made by sequentially depositing a negative electrode material, an organic material layer, and a positive electrode material on a substrate (International Publication No. 2003/012890). However, the manufacturing method is not limited thereto.

In an exemplary embodiment of the present specification, the first electrode is a positive electrode, and the second electrode is a negative electrode.

In another exemplary embodiment, the first electrode is a negative electrode, and the second electrode is a positive electrode.

As the positive electrode material, a material having a large work function is usually preferred so as to smoothly inject holes into an organic material layer. Specific examples of the positive electrode material which may be used in the present invention include: a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; an electrically conductive polymer, such as poly(3-methylthiophene), poly [3,4-(ethylene-1,2-dioxy)thiophene] (PEDOT), polypyrrole, and polyaniline, and the like, but are not limited thereto.

As the negative electrode material, a material having a small work function is usually preferred so as to smoothly inject electrons into an organic material layer. Specific examples of the negative electrode material include: a metal, such as magnesium, calcium, sodium, potassium, titanium, indium, yttrium, lithium, gadolinium, aluminum, silver, tin, and lead, or alloys thereof; a multi-layered structural material, such as LiF/Al or $LiO_2$/Al, and the like, but are not limited thereto.

The hole injection material is a layer which injects holes from an electrode, and is preferably a compound which has a capability of transporting holes and thus has an effect of injecting holes at a positive electrode and an excellent effect of injecting holes for a light emitting layer or a light emitting material, prevents excitons produced from the light emitting layer from moving to an electron injection layer or an electron injection material, and is also excellent in the ability to form a thin film. It is preferred that the highest occupied molecular orbital (HOMO) of the hole injection material is between the work function of the positive electrode material and the HOMO of a peripheral organic material layer. Specific examples of the hole injection material include metal porphyrin, oligothiophene, an arylamine-based organic material, a hexanitrile hexaazatriphenylene-based organic material, a quinacridone-based organic material, a perylene-based organic material, anthraquinone, a polyaniline and polythiophene-based electrically conductive polymer, and the like, but are not limited thereto.

The hole transporting layer is a layer which receives holes from a hole injection layer and transports holes to a light emitting layer, and a hole transporting material is suitably a material which may receive holes from a positive electrode or a hole injection layer to transfer holes to a light emitting layer, and has a large mobility for the holes. Specific examples thereof include an arylamine-based organic material, an electrically conductive polymer, a block copolymer in which a conjugate portion and a non-conjugate portion are present together, and the like, but are not limited thereto.

The light emitting material is a material which may receive holes and electrons from a hole transporting layer and an electron transporting layer, respectively, and combine the holes and the electrons to emit light in a visible ray region, and is preferably a material having good quantum efficiency to fluorescence or phosphorescence. Specific examples thereof include: a 8-hydroxy-quinoline aluminum complex ($Alq_3$); a carbazole-based compound; a dimerized styryl compound; BAlq; a 10-hydroxybenzoquinoline-metal compound; a benzoxazole, benzthiazole and benzimidazole-based compound; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensed aromatic ring derivative, or a hetero ring-containing compound, and the like. Specifically, examples of the condensed aromatic ring derivative include an anthracene derivative, a pyrene derivative, a naphthalene derivative, a pentacene derivative, a phenanthrene compound, a fluoranthene compound, and the like, and examples of the hetero ring-containing compound include a carbazole derivative, a dibenzofuran derivative, a ladder-type furan compound, a pyrimidine derivative, and the like, but the examples thereof are not limited thereto.

Examples of the dopant material include an aromatic amine derivative, a styrylamine compound, a boron complex, a fluoranthene compound, a metal complex, and the like. Specifically, the aromatic amine derivative is a condensed aromatic ring derivative having a substituted or unsubstituted arylamino group, and examples thereof include a pyrene, an anthracene, a chrysene, a periflanthene, and the like, which have an arylamino group, and the styrylamine compound is a compound in which a substituted or unsubstituted arylamine is substituted with at least one arylvinyl group, and one or two or more substituents selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transporting material is a material which receives electrons from an electron injection layer and transports the electrons to a light emitting layer, and an electron transporting material is a material which may inject electrons well from a negative electrode and may transfer the electrons to a light emitting layer, and is suitably a material which has large mobility for the electrons. Specific examples thereof include: an Al complex of 8-hydroxyquinoline; a complex including $Alq_3$; an organic radical compound; a hydroxyflavone-metal complex, and the like, but are not limited thereto. The electron transporting layer may be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a negative electrode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato) aluminum, tris(2-methyl-8-hydroxyquinolinato) aluminum, tris(8-hydroxyquinolinato) gallium, bis(10-hydroxybenzo[h]quinolinato) beryllium, bis(10-hydroxybenzo[h]quinolinato) zinc, bis(2-methyl-8-quinolinato) chlorogallium, bis(2-methyl-8-quinolinato) (o-cresolato) gallium, bis(2-methyl-8-quinolinato) (1-naphtholato) aluminum, bis(2-methyl-8-quinolinato) (2-naphtholato) gallium, and the like, but are not limited thereto.

The organic light emitting device according to the present specification may be a top emission type, a bottom emission type, or a dual emission type according to the material to be used.

In an exemplary embodiment of the present specification, the compound of Chemical Formula 1 may be included in an organic solar cell or an organic transistor in addition to an organic light emitting device.

The preparation of the compound represented by Chemical Formula 1 and the organic light emitting device including the same will be specifically described in the following Examples. However, the following Examples are provided for exemplifying the present specification, and the scope of the present specification is not limited thereby.

PREPARATION EXAMPLES

<Synthesis Example 1>—Preparation of Compound Represented by Compound 1

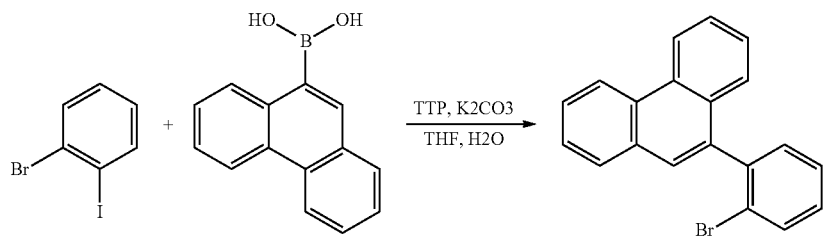

(Chemical Formula 1A)

-continued
(Chemical Formula 1B)
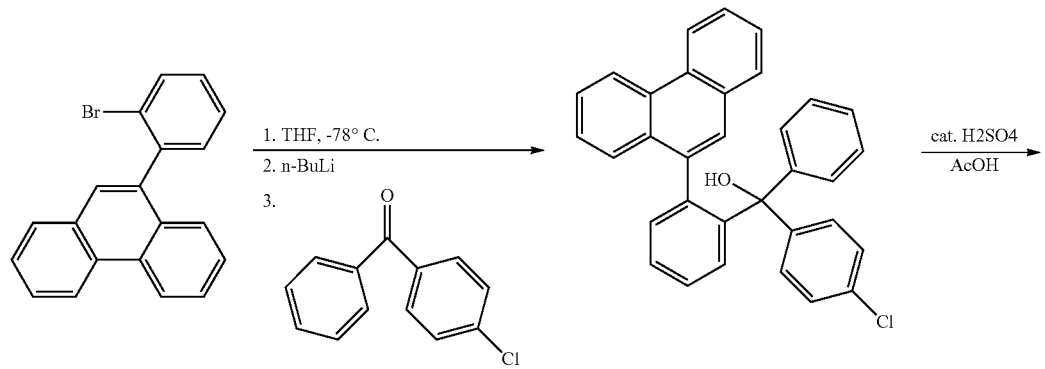
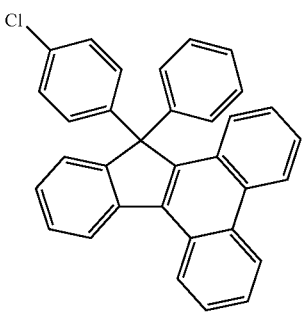
(Chemical Formula 1C)
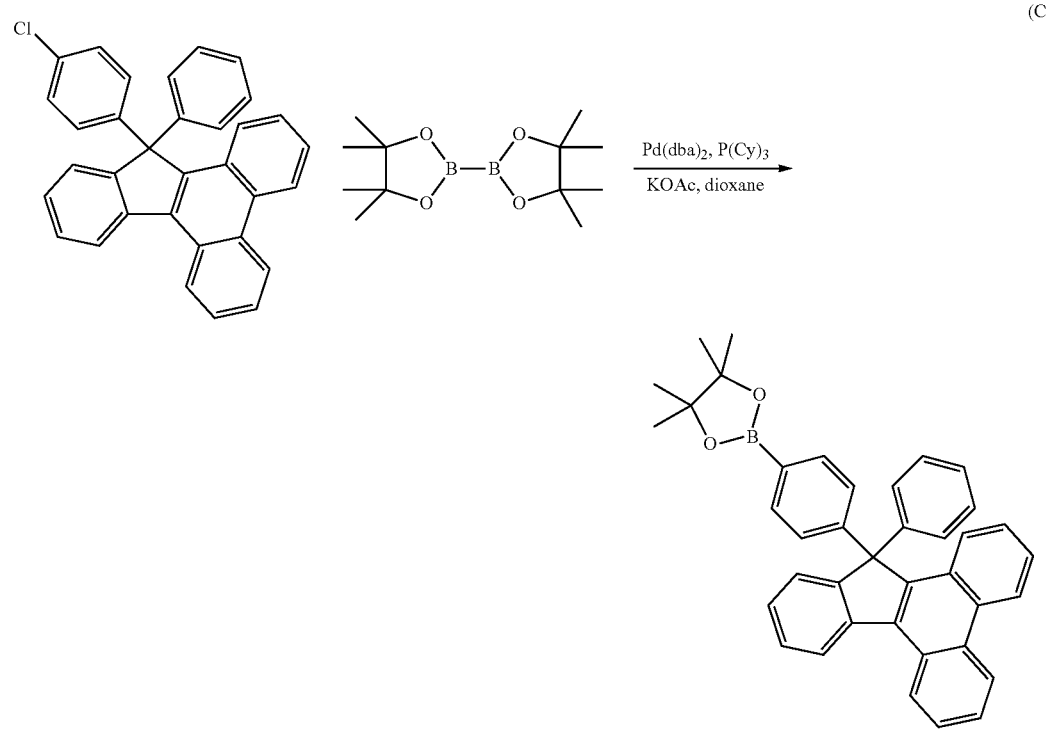

-continued (Chemical Formula 1D)

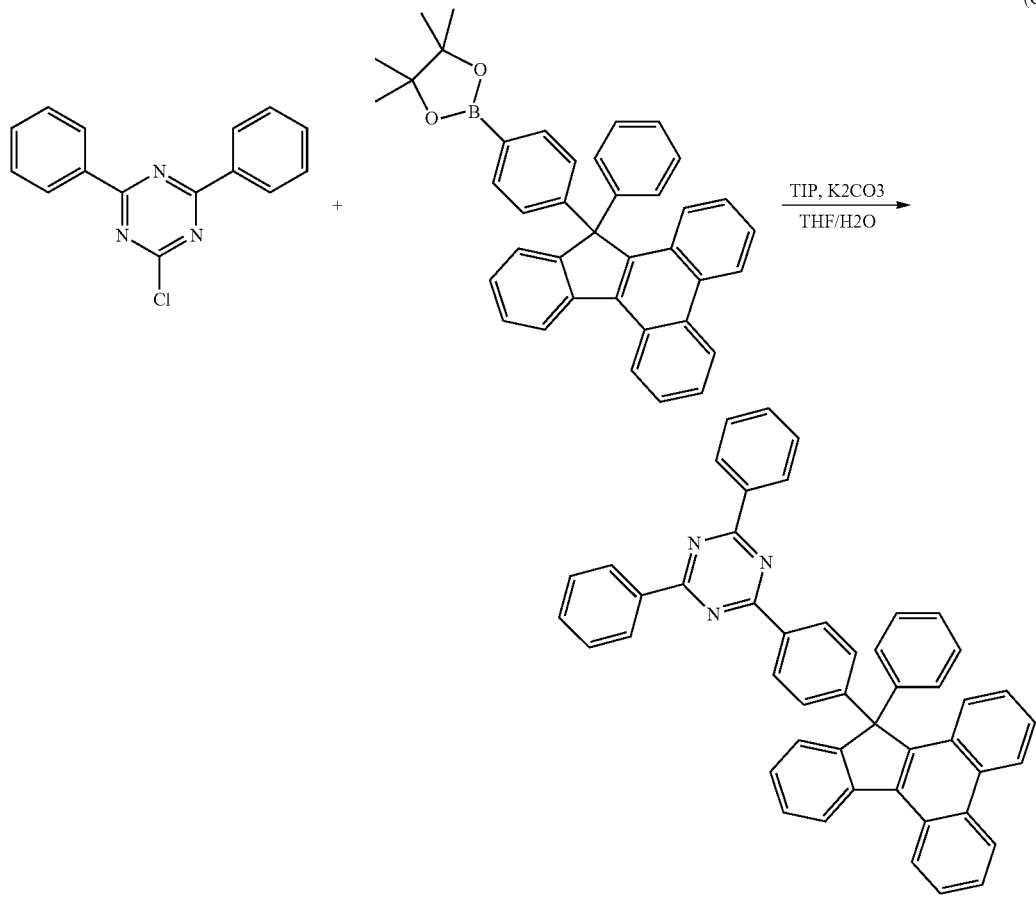

(Compound 1)

(1) Preparation of Chemical Formula 1A 1-bromo-2-iodobenzene (100.0 g, 353.47 mmol) and phenanthrene-yl-boronic acid (78.5 g, 353.47 mmol) were put into 500 ml of tetrahydrofuran under nitrogen atmosphere, and the resulting mixture was stirred and refluxed. Thereafter, potassium carbonate (97.7 g, 706.94 mmol) was dissolved in 300 ml of water, the resulting solution was introduced thereinto, the resulting mixture was sufficiently stirred, and then tetrakistriphenyl-phosphinopalladium (12.25 g, 10.60 mmol) was introduced thereinto. After the reaction for 12 hours, the temperature of the mixture was lowered to normal temperature, and the organic layer and the aqueous layer were separated. After the separation, the organic solvent was removed by distillation under reduced pressure, and then extraction was performed with chloroform and water, and then the organic layer was dried by using magnesium sulfate. Thereafter, the organic layer was distilled under reduced pressure, and then recrystallized by using ethanol. The produced solid was filtered and then dried to prepare Compound 1A (80.1 g, 68%). 1-bromo-2-iodobenzene (100.0 g, 353.47 mmol) and phenanthrene-9-yl-boronic acid were purchased from Aldrich Inc. and TCI Co., Ltd., respectively.

(2) Preparation of Chemical Formula 1B

Chemical Formula 1A (23.4 g, 70.22 mmol) was put into 300 ml of anhydrous tetrahydrofuran, and cooled to −78° C. Thereafter, n-butyl lithium (35.5 mL, 91.29 mmol) was slowly added dropwise thereto over 30 minutes while the mixture was being stirred, and then the resulting mixture was reacted for 1 hour. Thereafter, (4-chlorophenyl) (phenyl)methanone was introduced thereinto in a solid state, the temperature was slowly increased to normal temperature, and the resulting mixture was reacted for 4 hours. After the reaction, the reaction was terminated by pouring water thereto, and then the aqueous layer and the organic layer were separated, and then the organic layer was distilled under reduced pressure to obtain a solid. The solid was again put into 300 ml of acetic acid while the mixture was being stirred, and one or two drops of sulfuric acid was(were) introduced thereinto as a catalyst, and then the resulting mixture was refluxed. After the mixture was reacted for 2 hours, the produced solid was filtered, and the filtered material was again dissolved in chloroform, and then was neutralized and extracted by using water saturated with calcium carbonate, and then the organic layer was dried by using magnesium sulfate. Thereafter, the organic layer was distilled under reduced pressure, and then recrystallized by using ethanol. The produced solid was filtered and then dried to prepare Compound 1B (22.4 g, 70%). n-butyl lithium and (4-chlorophenyl) (phenyl)methanone were purchased from Aldrich Inc., and TCI Co., Ltd., respectively.

(3) Preparation of Chemical Formula 1C

Chemical Formula 1B (22.4 g, 49.45 mmol), bis(pinacolato)diboron (13.8 g, 54.40 mmol), and potassium acetate (14.6 g, 148.35 mmol) were mixed under nitrogen atmosphere, and the resulting mixture was added to 200 ml of dioxane, and heated while being stirred. Bis(dibenzylideneacetone)palladium (0.9 g, 1.48 mmol) and tricyclohexylphosphine (0.8 mg, 1.48 mmol) were added to the mixture, which was being, and the mixture was heated and stirred for 48 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Compound 1C (24.6 g, 91%).

(4) Preparation of Compound 1

Chemical Formula 1D (6.0 g, 22.41 mmol) and Chemical Formula 1C (12.8 g, 23.53 mmol) were put into 60 ml of tetrahydrofuran under nitrogen atmosphere, and the resulting mixture was stirred and refluxed. Thereafter, potassium carbonate (9.3 g, 67.23 mmol) was dissolved in 20 ml of water, the resulting solution was introduced thereinto, the resulting mixture was sufficiently stirred, and then tetrakis-triphenyl-phosphinopalladium (0.8 g, 0.67 mmol) was introduced thereinto. After the reaction for 8 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 1 (10.0 g, 67%). Chemical Formula 1D was purchased from Alpha Aesar.

MS: [M+H]+=649

<Synthesis Example 2>—Preparation of Compound Represented by Compound 2

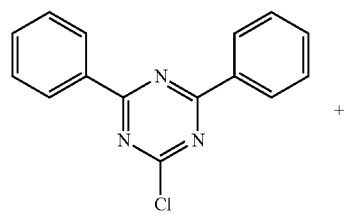

(Chemical Formula 2A)

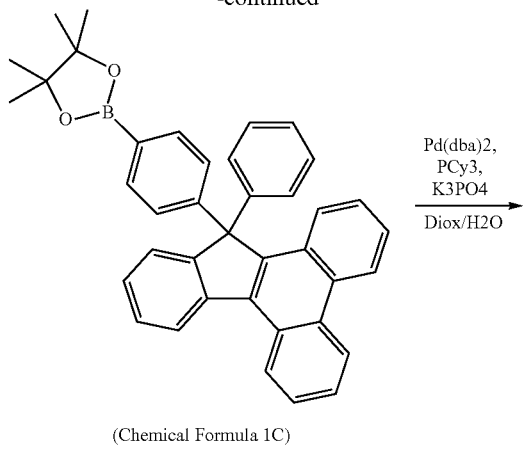

(Chemical Formula 1C)

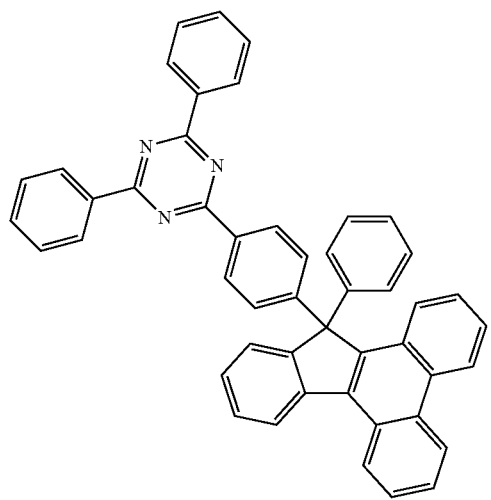

(Compound 2)

Chemical Formula 1C (5.5 g, 20.62 mmol) in Synthesis Example 1 and Chemical Formula 2A (11.8 g, 21.65 mmol) were put into 60 ml of dioxane under nitrogen atmosphere, and the resulting mixture was stirred and refluxed. Thereafter, potassium phosphate (14.0 g, 61.86 mmol) was dissolved in 20 ml of water, the resulting solution was introduced thereinto, the resulting mixture was sufficiently stirred, and then bis(dibenzylidineacetone)palladium (0.4 g, 0.62 mmol) and tricyclohexylphosphine (0.3 mg, 1.24 mmol) were dissolved in dioxane, and the resulting solution was introduced thereinto. After the reaction for 24 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 2 (10.0 g, 67%). Chemical Formula 2A was purchased from Alpha Aesar.

MS: [M+H]+=648
<Synthesis Example 3>—Preparation of Compound Represented by Compound 3
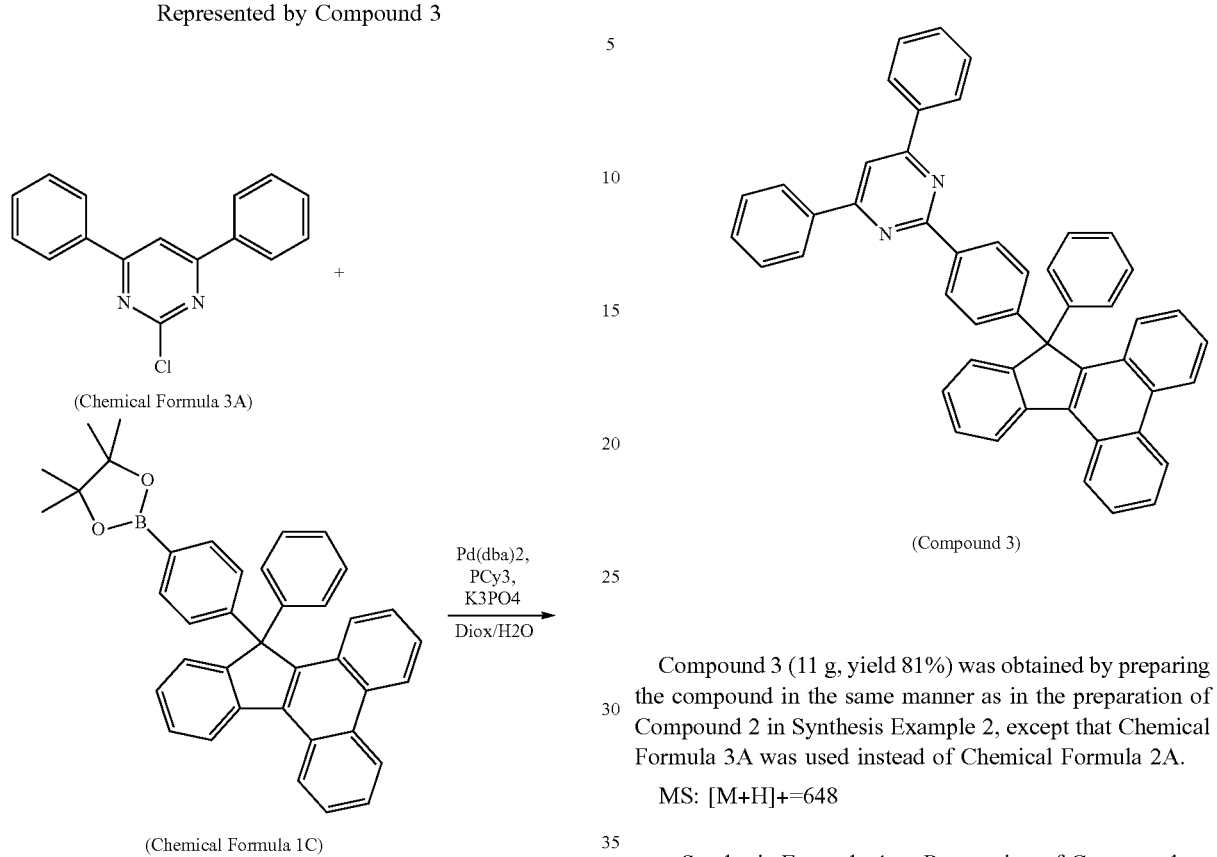
Compound 3 (11 g, yield 81%) was obtained by preparing the compound in the same manner as in the preparation of Compound 2 in Synthesis Example 2, except that Chemical Formula 3A was used instead of Chemical Formula 2A.
MS: [M+H]+=648
<Synthesis Example 4>—Preparation of Compound Represented by Compound 7
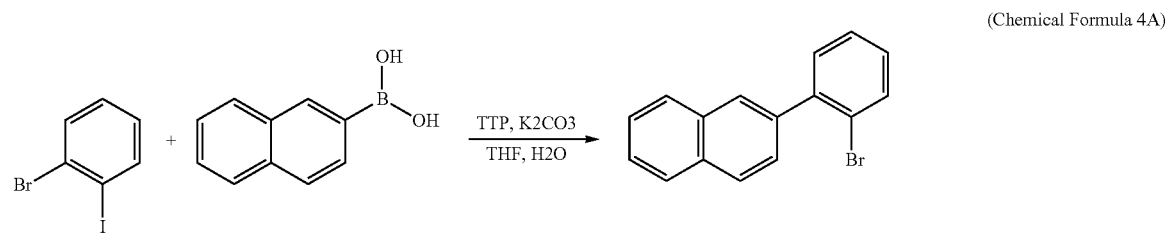
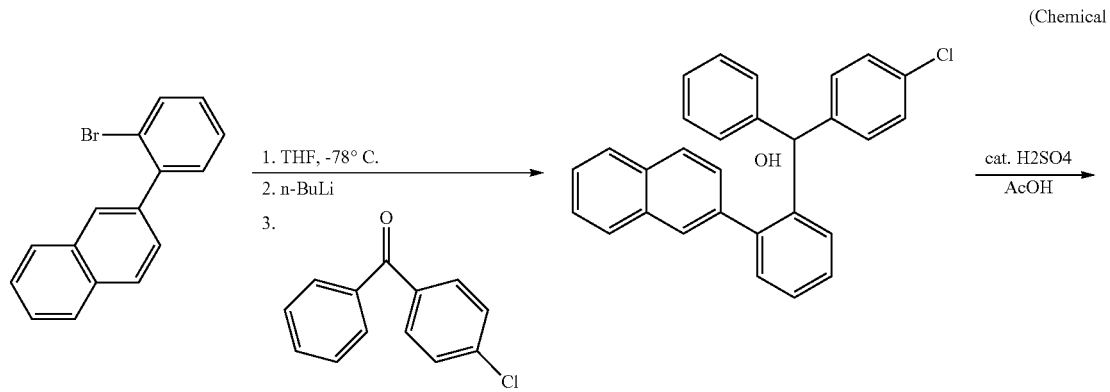

-continued
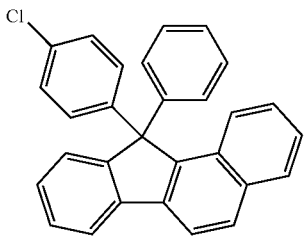
(Chemical Formula 4C)
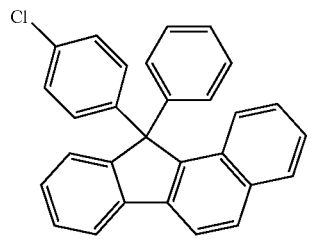 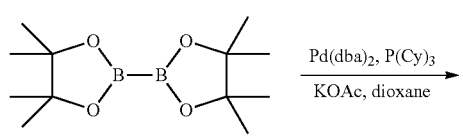
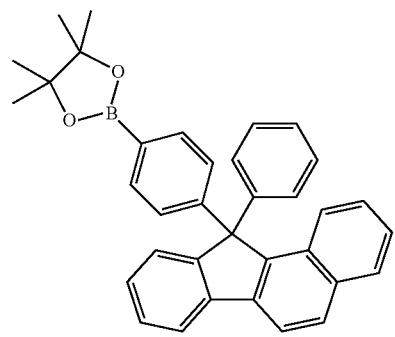
(Chemical Formula 1D)
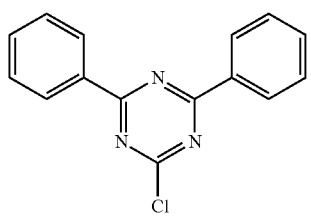 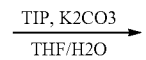 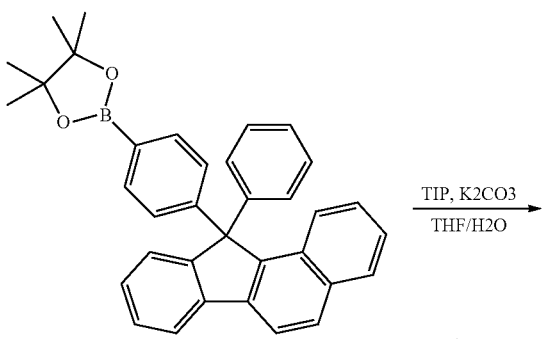
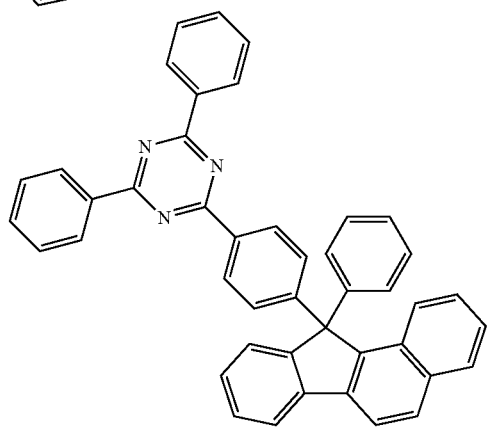
(Compound 7)

(1) Preparation of Chemical Formula 4A 1-bromo-2-iodobenzene (100.0 g, 353.47 mmol) and naphthalene-2-yl-boronic acid (30.4 g, 176.73 mmol) were put into 400 ml of tetrahydrofuran under nitrogen atmosphere, and the resulting mixture was stirred and refluxed. Thereafter, potassium carbonate (48.9 g, 353.47 mmol) was dissolved in 200 ml of water, the resulting solution was introduced thereinto, the resulting mixture was sufficiently stirred, and then tetrakistriphenyl-phosphinopalladium (6.12 g, 5.30 mmol) was introduced thereinto. After the reaction for 18 hours, the temperature of the mixture was lowered to normal temperature, and the organic layer and the aqueous layer were separated. After the separation, the organic solvent was removed by distillation under reduced pressure, and then extraction was performed with chloroform and water, and then the organic layer was dried by using magnesium sulfate. Thereafter, the organic layer was distilled under reduced pressure, and then recrystallized by using ethanol. The produced solid was filtered and then dried to prepare Chemical Formula 4A (63.6 g, 54%). 1-bromo-2-iodobenzene (100.0 g, 353.47 mmol) and naphthalene-2-yl-boronic acid were purchased from Aldrich Inc. and TCI Co., Ltd., respectively.

(2) Preparation of Chemical Formula 4B

Chemical Formula 4A (50.0 g, 176.57 mmol) was put into 500 ml of anhydrous tetrahydrofuran, and cooled to −78° C. Thereafter, n-butyl lithium (91.8 mL, 229.54 mmol) was slowly added dropwise thereto over 60 minutes while the mixture was being stirred, and then the resulting mixture was reacted for 1 hour. Thereafter, (4-chlorophenyl) (phenyl)methanone was introduced thereinto in a solid state, the temperature was slowly increased to normal temperature, and the resulting mixture was reacted for 2 hours. After the reaction, the reaction was terminated by pouring water thereto, and then the aqueous layer and the organic layer were separated, and then the organic layer was distilled under reduced pressure to obtain a solid. The solid was again put into 500 ml of acetic acid while the mixture was being stirred, and one or two drops of sulfuric acid was(were) introduced thereinto as a catalyst, and then the resulting mixture was refluxed. After the mixture was reacted for 2 hours, the produced solid was filtered, and the filtered material was again dissolved in chloroform, and then was neutralized and extracted by using water saturated with calcium carbonate, and then the organic layer was dried by using magnesium sulfate. Thereafter, the organic layer was distilled under reduced pressure, and then recrystallized by using ethanol. The produced solid was filtered and then dried to prepare Chemical Formula 4B (45.5 g, 64%). n-butyl lithium and (4-chlorophenyl) (phenyl)methanone were purchased from Aldrich Inc., and TCI Co., Ltd., respectively.

(3) Preparation of Chemical Formula 4C

Chemical Formula 4B (45.5 g, 112.93 mmol), bis(pinacolato)diboron (31.5 g, 124.22 mmol), and potassium acetate (33.2 g, 338.78 mmol) were mixed under nitrogen atmosphere, and the resulting mixture was added to 500 ml of dioxane, and heated while being stirred. Bis(dibenzylideneacetone)palladium (1.9 g, 3.39 mmol) and tricyclohexylphosphine (1.9 mg, 6.78 mmol) were added to the mixture, which was being refluxed, and the mixture was heated and stirred for 60 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Chemical Formula 4C (52.5 g, 94%).

(4) Preparation of Compound 7

Chemical Formula 1D (6.0 g, 22.41 mmol) and Chemical Formula 4C (12.9 g, 23.53 mmol) were put into 60 ml of tetrahydrofuran under nitrogen atmosphere, and the resulting mixture was stirred and refluxed. Thereafter, potassium carbonate (9.3 g, 67.23 mmol) was dissolved in 30 ml of water, the resulting solution was introduced thereinto, the resulting mixture was sufficiently stirred, and then tetrakistriphenyl-phosphinopalladium (0.8 g, 0.67 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 7 (9.0 g, 67%). Chemical Formula 1D was purchased from Alpha Aesar.

MS: [M+H]+=599

<Synthesis Example 5>—Preparation of Compound Represented by Compound 10

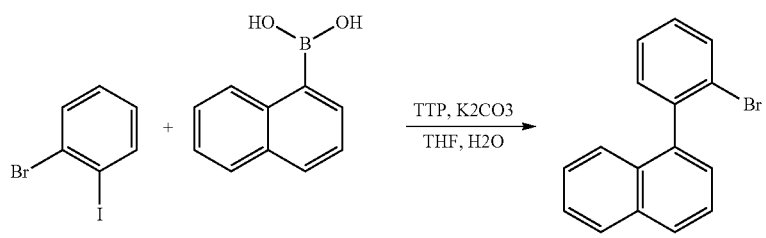

(Chemical Formula 5A)

-continued
(Chemical Formula 5B)
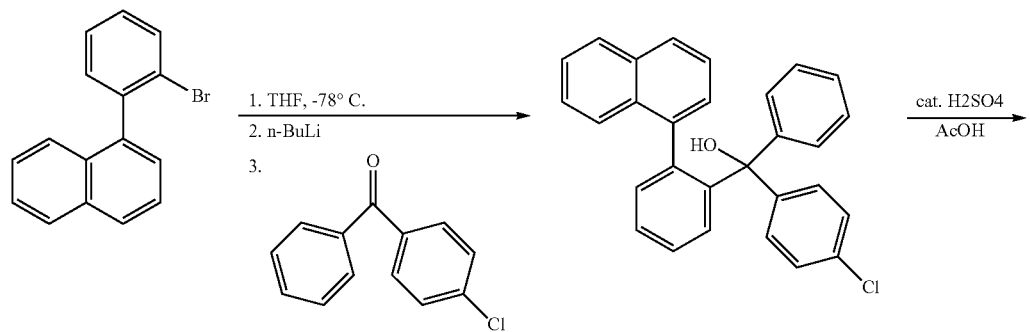
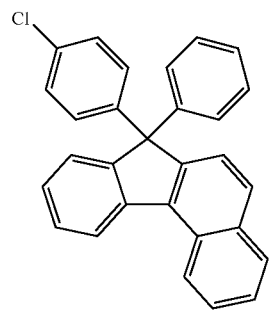
(Chemical Formula 5C)
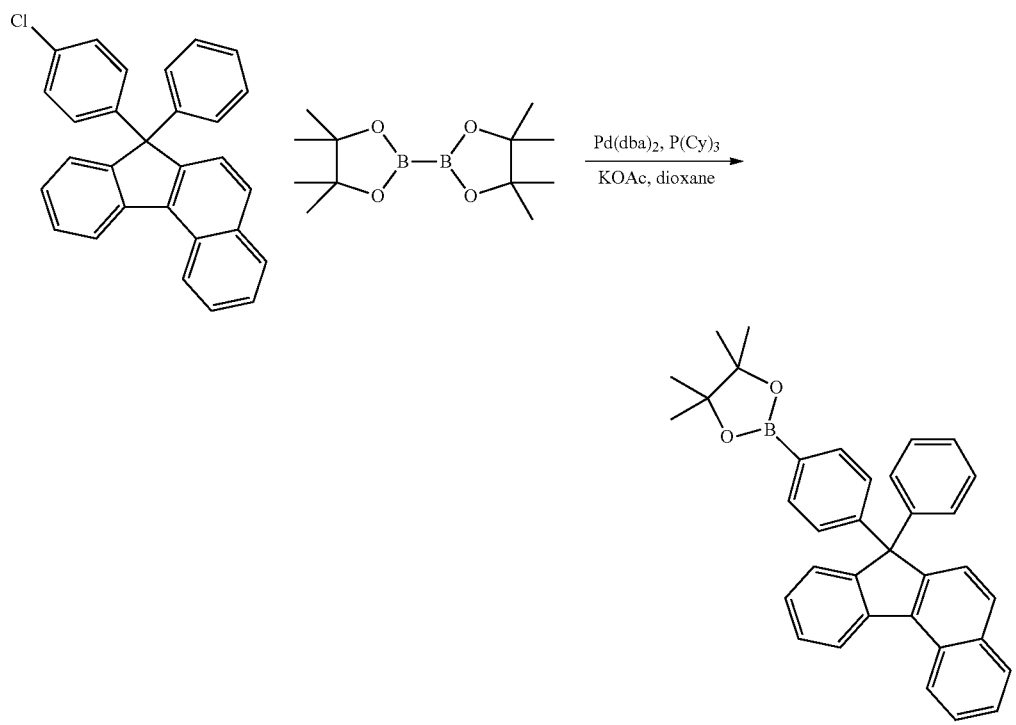

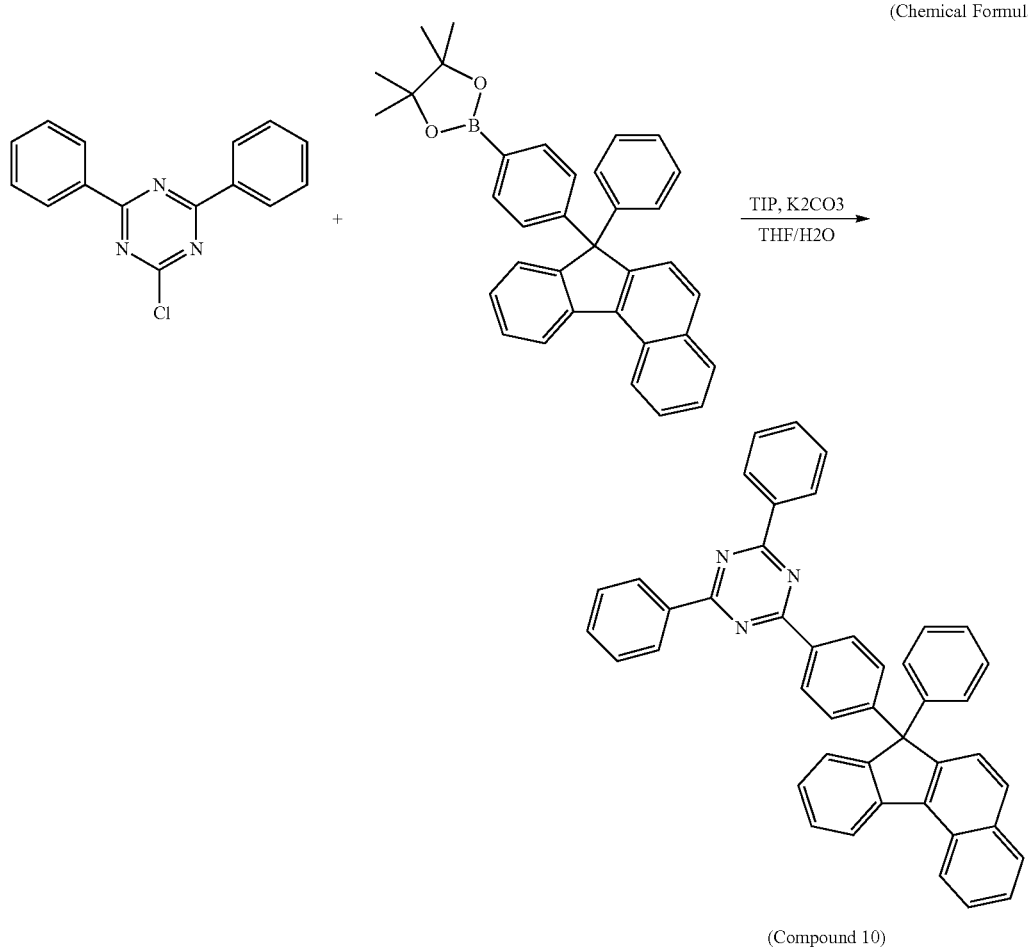

(Chemical Formula 1D)

(Compound 10)

(1) Preparation of Chemical Formula 5A 1-bromo-2-iodobenzene (100.0 g, 353.47 mmol) and naphthalene-1-yl-boronic acid (30.4 g, 176.73 mmol) were put into 400 ml of tetrahydrofuran under nitrogen atmosphere, and the resulting mixture was stirred and refluxed. Thereafter, potassium carbonate (48.9 g, 353.47 mmol) was dissolved in 200 ml of water, the resulting solution was introduced thereinto, the resulting mixture was sufficiently stirred, and then tetrakistriphenyl-phosphinopalladium (6.12 g, 5.30 mmol) was introduced thereinto. After the reaction for 18 hours, the temperature of the mixture was lowered to normal temperature, and the organic layer and the aqueous layer were separated. After the separation, the organic solvent was removed by distillation under reduced pressure, and then extraction was performed with chloroform and water, and then the organic layer was dried by using magnesium sulfate. Thereafter, the organic layer was distilled under reduced pressure, and then recrystallized by using ethanol. The produced solid was filtered and then dried to prepare Chemical Formula 5A (80.1 g, 68%). 1-bromo-2-iodobenzene (100.0 g, 353.47 mmol) and phenanthrene-9-yl-boronic acid were purchased from Aldrich Inc., and TCI Co., Ltd., respectively.

(2) Preparation of Chemical Formula 5B

Chemical Formula 5A (50.0 g, 176.57 mmol) was put into 500 ml of anhydrous tetrahydrofuran, and cooled to −78° C. Thereafter, n-butyl lithium (91.8 mL, 229.54 mmol) was slowly added dropwise thereto over 60 minutes while the mixture was being stirred, and then the resulting mixture was reacted for 1 hour. Thereafter, (4-chlorophenyl) (phenyl)methanone was introduced thereinto in a solid state, the temperature was slowly increased to normal temperature, and the resulting mixture was reacted for 2 hours. After the reaction, the reaction was terminated by pouring water thereto, and then the aqueous layer and the organic layer were separated, and then the organic layer was distilled under reduced pressure to obtain a solid. The solid was again put into 500 ml of acetic acid while the mixture was being stirred, and one or two drops of sulfuric acid was(were) introduced thereinto as a catalyst, and then the resulting mixture was refluxed. After the mixture was reacted for 2 hours, the produced solid was filtered, and the filtered material was again dissolved in chloroform, and then was neutralized and extracted by using water saturated with calcium carbonate, and then the organic layer was dried by using magnesium sulfate. Thereafter, the organic layer was distilled under reduced pressure, and then recrystallized by using ethanol. The produced solid was filtered and then dried to prepare Chemical Formula 5B (54.8 g, 77%). n-butyl lithium and (4-chlorophenyl) (phenyl)methanone were purchased from Aldrich Inc., and TCI Co., Ltd., respectively.

(3) Preparation of Chemical Formula 5C

Chemical Formula 5B (54.8 g, 136.01 mmol), bis(pinacolato)diboron (38.0 g, 149.61 mmol), and potassium acetate (40.0 g, 408.02 mol) were mixed under nitrogen atmosphere, and the resulting mixture was added to 500 ml of dioxane, and heated while being stirred. Bis(dibenzylideneacetone)palladium (2.3 g, 4.08 mmol) and tricyclohexylphosphine (2.3 mg, 8.16 mmol) were added to the mixture, which was being refluxed, and the mixture was heated and stirred for 60 hours. After the reaction was terminated, the temperature of the mixture was lowered to normal temperature, and then the mixture was filtered. Water was poured into the filtrate, extraction was performed with chloroform, and the organic layer was dried over anhydrous magnesium sulfate. After distillation under reduced pressure, recrystallization was performed with ethanol to prepare Chemical Formula 5C (59.2 g, 88%).

(4) Preparation of Compound 10

Chemical Formula 1D (6.0 g, 22.41 mmol) and Chemical Formula 5C (12.9 g, 23.53 mmol) were put into 60 ml of tetrahydrofuran under nitrogen atmosphere, and the resulting mixture was stirred and refluxed. Thereafter, potassium carbonate (9.3 g, 67.23 mmol) was dissolved in 30 ml of water, the resulting solution was introduced thereinto, the resulting mixture was sufficiently stirred, and then tetrakis-triphenyl-phosphinopalladium (0.8 g, 0.67 mmol) was introduced thereinto. After the reaction for 12 hours, the temperature of the mixture was lowered to normal temperature and the mixture was filtered. The filtered material was extracted with chloroform and water, and then the organic layer was dried by using magnesium sulfate. Thereafter, the organic layer was distilled under reduced pressure, and then recrystallized by using ethyl acetate. The produced solid was filtered and then dried to prepare Compound 10 (7.4 g, 55%). Chemical Formula 1D was purchased from Alpha Aesar.

MS: [M+H]+=599

EXAMPLES

Experimental Example 1-1

A glass substrate (Corning 7059 glass) thinly coated with ITO (indium tin oxide) to have a thickness of 1000 Å was put into distilled water in which a dispersant was dissolved, and ultrasonically washed. A product manufactured by Fischer Co., was used as the detergent, and distilled water filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents in this order, and drying was then conducted.

Hexanitrile hexaazatriphenylene was thermally vacuum deposited to have a thickness of 500 Å on a transparent ITO electrode, which was thus prepared, thereby forming a hole injection layer. HT1 (400 Å), which is a material transporting holes, was vacuum deposited thereon, and then the host H1 and the dopant D1 compound were vacuum deposited as a light emitting layer to have a thickness of 300 Å. Compound 1 prepared in Synthesis Example 1 and LiQ (lithium quinolate) were vacuum deposited at a weight ratio of 1:1 on the light emitting layer, thereby forming an electron injection and transporting layer having a thickness of 350 Å. Lithium fluoride (LiF) and aluminum were sequentially deposited to have a thickness of 12 Å and 2,000 Å, respectively, on the electron injection and transporting layer, thereby forming a negative electrode to manufacture an organic light emitting device.

In the aforementioned procedure, the deposition rate of the organic material was maintained at 0.4 to 0.7 Å/sec, the deposition rates of lithium fluoride and aluminum of the negative electrode were maintained at 0.3 Å/sec and at 2 Å/sec, respectively, and the degree of vacuum during the deposition was maintained at $2 \times 10^{-7}$ to $5 \times 10^{-6}$ torr, thereby manufacturing an organic light emitting device.

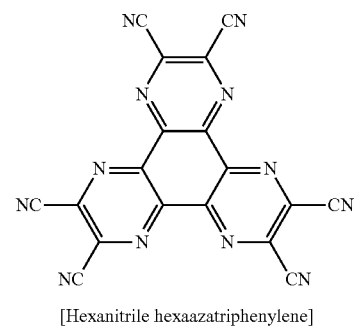

[Hexanitrile hexaazatriphenylene]

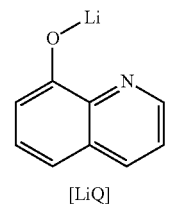

[LiQ]

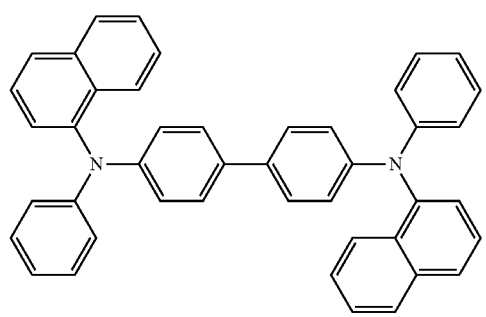

[HT1]

[H1]

-continued

[D1]

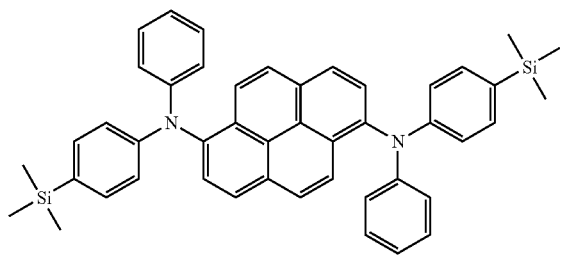

Experimental Example 1-2

An experiment was performed in the same manner as in Experimental Example 1-1, except that as the electron transporting layer, Compound 2 was used instead of Compound 1.

Experimental Example 1-3

An experiment was performed in the same manner as in Experimental Example 1-1, except that as the electron transporting layer, Compound 3 was used instead of Compound 1.

Experimental Example 1-4

An experiment was performed in the same manner as in Experimental Example 1-1, except that as the electron transporting layer, Compound 7 was used instead of Compound 1.

Experimental Example 1-5

An experiment was performed in the same manner as in Experimental Example 1-1, except that as the electron transporting layer, Compound 10 was used instead of Compound 1.

Experimental Example 2-1

A glass substrate thinly coated with indium tin oxide (ITO) to have a thickness of 1,500 Å was put into distilled water in which a detergent was dissolved, and ultrasonically washed. In this case, a product manufactured by the Fischer Co., was used as the detergent, and distilled water twice filtered using a filter manufactured by Millipore Co., was used as the distilled water. After the ITO was washed for 30 minutes, ultrasonic washing was conducted repeatedly twice using distilled water for 10 minutes. After the washing using distilled water was completed, ultrasonic washing was conducted using isopropyl alcohol, acetone, and methanol solvents, and drying was conducted, and then the product was transferred to a plasma cleaner. In addition, the substrate was cleaned using oxygen plasma for 5 minutes, and then transferred to a vacuum evaporator.

Hexanitrile hexaazatriphenylene (HAT) of the following Chemical Formula was thermally vacuum deposited to have a thickness of 500 Å on a transparent ITO electrode, which was thus prepared, thereby forming a hole injection layer.

[HAT]

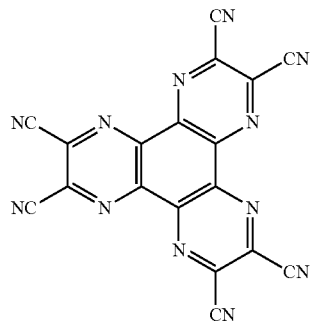

An N, N-bis-(1-naphthalenyl)-N, N-bis-phenyl-(1, 1-biphenyl)-4, 4-diamine (NPB) compound having the following structure was thermally vacuum deposited to have a thickness of 400 Å on the hole injection layer, thereby forming a hole transporting layer.

[NPB]

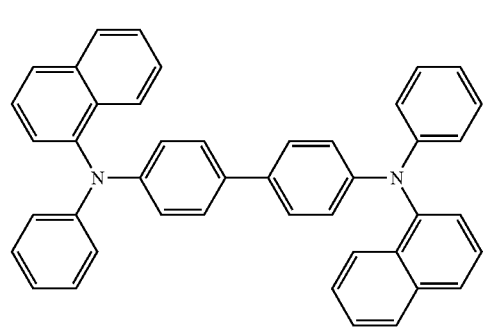

Subsequently, Compound 1 prepared in Synthesis Example 1 was vacuum deposited to have a film thickness of 300 Å at a concentration of 10% with respect to an Ir(ppy)₃ dopant on the hole transporting layer, thereby forming a light emitting layer.

An electron transporting material as described below was vacuum deposited to have a thickness of 200 Å on the light emitting layer, thereby forming a layer which injects and transports electrons.

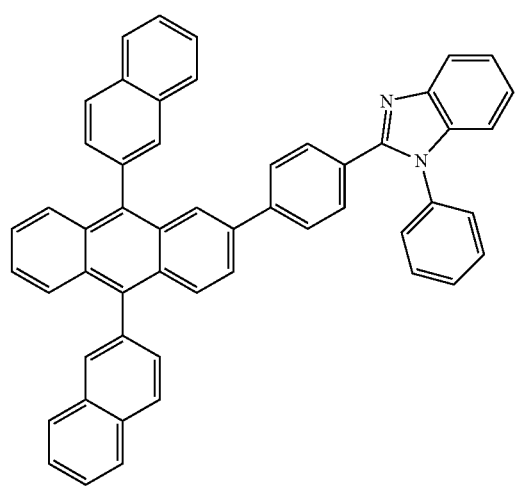

[Electron Transporting Material]

Lithium fluoride (LiF) and aluminum were sequentially deposited to have a thickness of 12 Å and 2,000 Å, respectively, on the layer which injects and transports electrons, thereby forming a negative electrode.

In the aforementioned procedure, the deposition rate of the organic material was maintained at 0.4 to 0.7 Å/sec, the deposition rates of lithium fluoride and aluminum of the negative electrode were maintained at 0.3 Å/sec, and at 2 Å/sec, respectively, and the degree of vacuum during the deposition was maintained at $2 \times 10^7$ to $5 \times 10^8$ torr.

Experimental Example 2-2

An experiment was performed in the same manner as in Experimental Example 2-1, except that as the light emitting layer, Compound 3 was used instead of Compound 1.

Experimental Example 2-3

An experiment was performed in the same manner as in Experimental Example 2-1, except that as the light emitting layer, Compound 7 was used instead of Compound 1.

Experimental Example 2-4

An experiment was performed in the same manner as in Experimental Example 2-1, except that as the light emitting layer, Compound 10 was used instead of Compound 1.

Comparative Example 1

An organic light emitting device was manufactured in the same manner as in Experimental Example 1-1, except that the compound of the following ET1 was used instead of Compound 1 in Experimental Example 1-1.

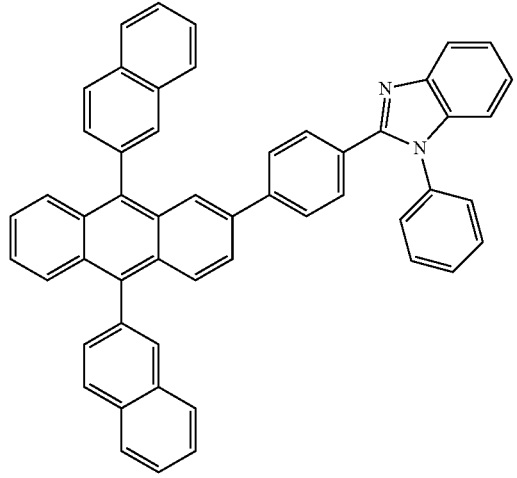

[ET1]

Comparative Example 2

An organic light emitting device was manufactured in the same manner as in Experimental Example 1-1, except that the compound of the following ET2 was used instead of Compound 1 in Experimental Example 1-1.

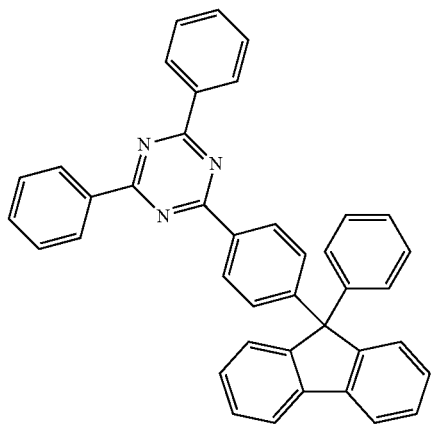

[ET2]

Comparative Example 3

An organic light emitting device was manufactured in the same manner as in Experimental Example 1-1, except that the compound of the following ET3 was used instead of Compound 1 in Experimental Example 1-1.

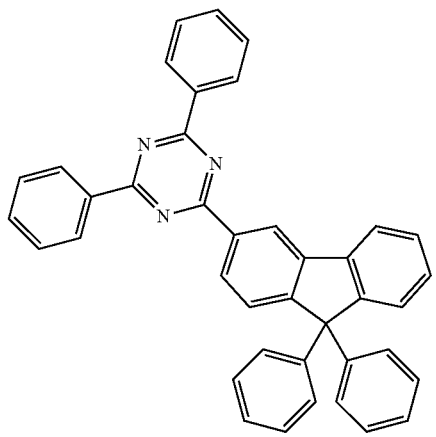

[ET3]

Comparative Example 4

An organic light emitting device was manufactured in the same manner as in Experimental Example 1-1, except that the compound of the following ET4 was used instead of Compound 1 in Experimental Example 1-1.

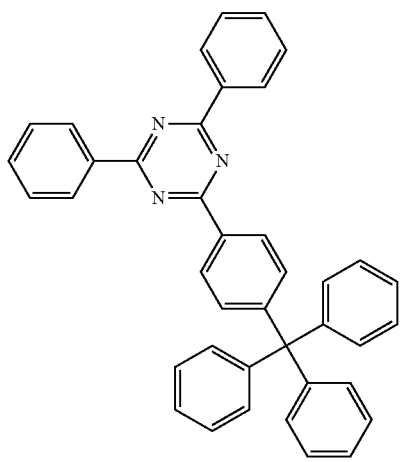

Comparative Example 5

An organic light emitting device was manufactured in the same manner as in Experimental Example 2-1, except that the compound of the following ET2 was used instead of Compound 1 in Experimental Example 2-1.

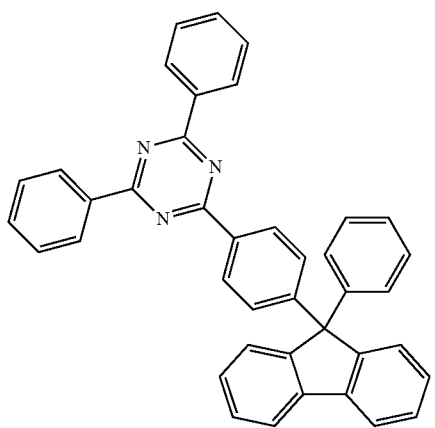

Comparative Example 6

An organic light emitting device was manufactured in the same manner as in Experimental Example 2-1, except that the compound of the following ET3 was used instead of Compound 1 in Experimental Example 2-1.

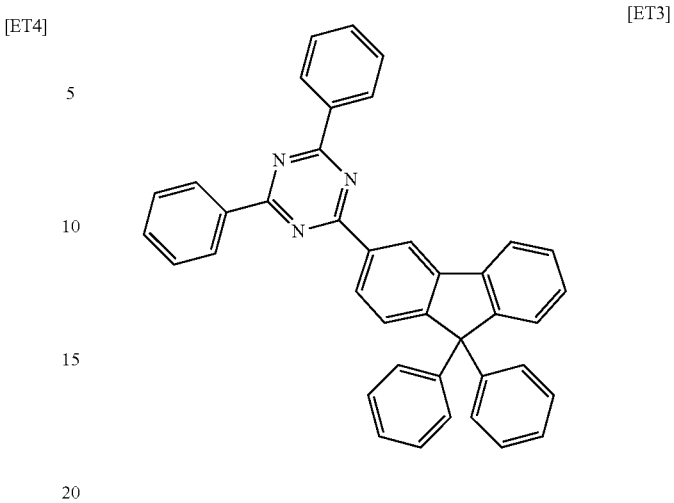

Comparative Example 7

An organic light emitting device was manufactured in the same manner as in Experimental Example 2-1, except that the compound of the following ET4 was used instead of Compound 1 in Experimental Example 2-1.

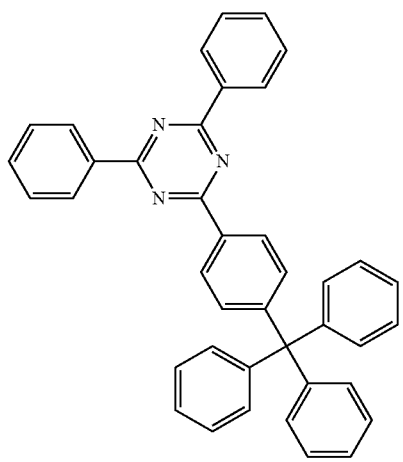

Comparative Example 8

An organic light emitting device was manufactured in the same manner as in Experimental Example 2-1, except that the compound of the following ET5 was used instead of Compound 1 in Experimental Example 2-1.

[ET5]

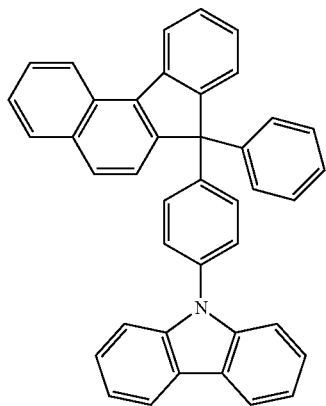

Comparative Example 9

An organic light emitting device was manufactured in the same manner as in Experimental Example 2-1, except that the compound of the following ET6 was used instead of Compound 1 in Experimental Example 2-1.

[ET6]

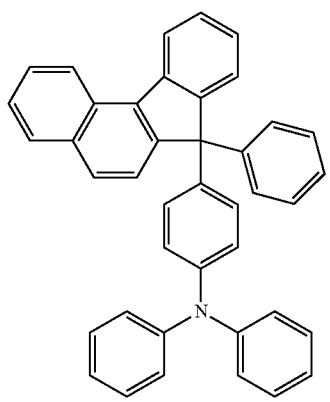

Comparative Example 10

An organic light emitting device was manufactured in the same manner as in Experimental Example 2-1, except that the compound of the following ET7 was used instead of Compound 1 in Experimental Example 2-1.

[ET7]

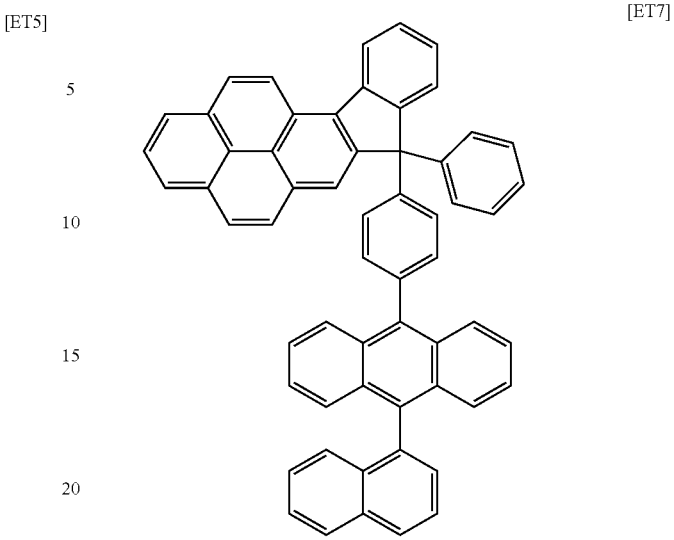

Comparative Example 11

An organic light emitting device was manufactured in the same manner as in Experimental Example 2-1, except that the compound of the following ET8 was used instead of Compound 1 in Experimental Example 2-1.

[ET8]

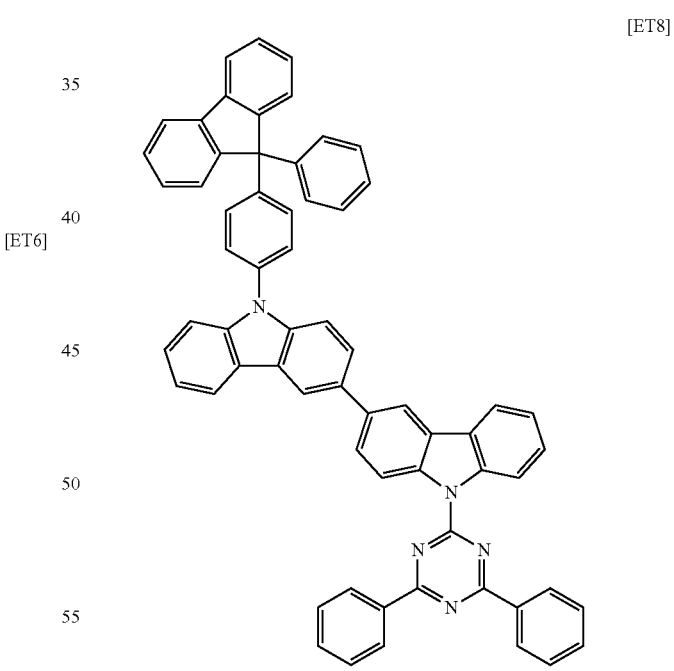

For the organic light emitting devices manufactured by using each compound as the electron transporting layer material as in Experimental Examples 1-1 to 1-5 and Comparative Examples 1 to 4, the driving voltage and the light emitting efficiency were measured at a current density of 10 mA/cm$^2$, and a time ($LT_{98}$) for reaching a 98% value compared to the initial luminance was measured at a current density of 20 mA/cm$^2$. The results are shown in the following Table 2.

Further, for the organic light emitting devices manufactured by using each compound as the light emitting layer material as in Experimental Examples 2-1 to 2-4 and Comparative Examples 5 to 11, the driving voltage and the light emitting efficiency were measured at a current density of 10 mA/cm$^2$, and a time ($LT_{98}$) for reaching a 98% value compared to the initial luminance was measured at a current density of 20 mA/cm$^2$. The results are shown in the following Table 1.

TABLE 1

| Experimental Example (at 10 mA/cm2) | Compound | Voltage (V) | Current Efficiency (cd/A) | Color Coordinate (x, y) | Life Time 98% at 20 mA/cm2 |
|---|---|---|---|---|---|
| Experimental Example 1-1 | Compound 1 | 3.93 | 6.5 | (0.134, 0.133) | 100 |
| Experimental Example 1-2 | Compound 2 | 3.88 | 7.0 | (0.134, 0.133) | 88 |
| Experimental Example 1-3 | Compound 3 | 3.90 | 6.91 | (0.134, 0.133) | 80 |
| Experimental Example 1-4 | Compound 7 | 3.94 | 6.76 | (0.134, 0.133) | 94 |
| Experimental Example 1-5 | Compound 10 | 3.85 | 6.88 | (0.134, 0.133) | 72 |
| Experimental Example 2-1 | Compound 1 (doping 10%) | 4.21 | 66.5 | (0.445, 0.543) | 120 |
| Experimental Example 2-2 | Compound 3 (doping 10%) | 4.35 | 62.4 | (0.450, 0.539) | 90 |
| Experimental Example 2-3 | Compound 7 (doping 10%) | 4.62 | 60.8 | (0.448, 0.544) | 110 |
| Experimental Example 2-4 | Compound 10 (doping 10%) | 4.44 | 64.2 | (0.455, 0.535) | 125 |
| Comparative Example 1 | ET1 | 3.96 | 5.67 | (0.134, 0.133) | 80 |
| Comparative Example 2 | ET2 | 3.90 | 6.80 | (0.132, 0.134) | 15 |
| Comparative Example 3 | ET3 | 3.86 | 6.52 | (0.133, 0.135) | 81 |
| Comparative Example 4 | ET4 | 4.22 | 7.45 | (0.134, 0.133) | 0.5 |
| Comparative Example 5 | ET2 (doping 10%) | 4.22 | 62.4 | (0.450, 0.539) | 30 |
| Comparative Example 6 | ET3 (doping 10%) | 4.23 | 60.8 | (0.448, 0.544) | 22 |
| Comparative Example 7 | ET4 (doping 10%) | 4.10 | 64.2 | (0.455, 0.535) | 9 |
| Comparative Example 8 | ET5 (doping 10%) | 5.22 | 30.5 | (0.450, 0.539) | 33 |
| Comparative Example 9 | ET6 (doping 10%) | 6.10 | 31.2 | (0.448, 0.544) | 44 |
| Comparative Example 10 | ET7 (doping 10%) | 7.14 | 14.2 | (0.555, 0.575) | 15 |
| Comparative Example 11 | ET8 (doping 10%) | 4.11 | 52.4 | (0.450, 0.539) | 90 |

As can be seen in Table 1, it can be seen that the organic light emitting device manufactured by using the compound of the present specification as the electron transporting layer material showed similar efficiency and exhibited excellent characteristics in terms of stability compared to the case where the materials of Comparative Examples 2 and 4 were used, and exhibited excellent characteristics in terms of efficiency when compared to the case where the materials of Comparative Examples 1 and 3 were used.

Further, it can be seen that the organic light emitting device manufactured by using the compound of the present specification as the light emitting layer material exhibited excellent characteristics in terms of efficiency and life time compared to the materials of Comparative Examples 5 to 11.

Although preferred exemplary embodiments of the present invention have been described, the present invention is not limited thereto, and various modifications can be made within the scope of the claims and the detailed description of the invention, and also belong to the scope of the invention.

EXPLANATION OF REFERENCE NUMERALS AND SYMBOLS

1: Substrate
2: Positive electrode
3: Light emitting layer
4: Negative electrode
5: Hole injection layer
6: Hole transporting layer
7: Light emitting layer
8: Electron transporting layer

The invention claimed is:

1. A hetero-cyclic compound of Chemical Formula 1:

[Chemical Formula 1]

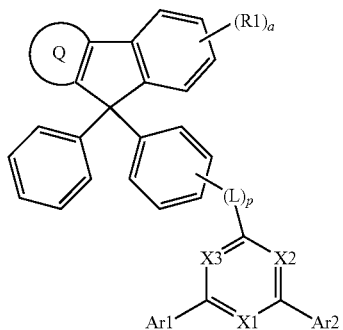

wherein in Chemical Formula 1:

X1 to X3 are the same as or different from each other, and are each independently CR or N, wherein at least two of X1 to X3 is N;

Q is a substituted or unsubstituted naphthyl group, a substituted or unsubstituted anthracenyl group, a substituted or unsubstituted pyrenyl group, a substituted or unsubstituted chrysenyl group, a substituted or unsubstituted fluoranthene group, a substituted or unsubstituted triphenylene group, a substituted or unsubstituted phenanthrenyl group, a substituted or unsubstituted dibenzothiophene group, a substituted or unsubstituted dibenzofuranyl group, or substituted or unsubstituted carbazole;

L is a direct bond, a substituted or unsubstituted arylene, or a substituted or unsubstituted heteroarylene;

R, R1, Ar1, and Ar2 are the same as or different from each other, and are each independently hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphine oxide group, a substituted or unsubstituted aryl group, or a substituted or unsubstituted hetero-cyclic group, or combine with an adjacent group to form a substituted or unsubstituted ring;

a is an integer of 0 to 4;

p is an integer of 0 to 5; and when a and p are each 2 or more, the structures in the parenthesis are the same as or different from each other.

2. The hetero-cyclic compound of claim 1, wherein Chemical Formula 1 is any one of the following Chemical Formulae 2 to 4:

[Chemical Formula 2]

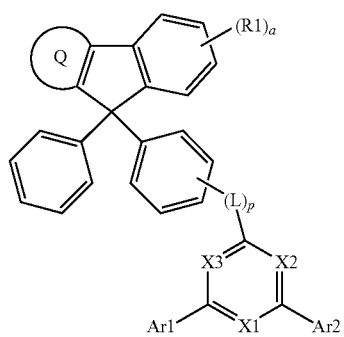

[Chemical Formula 3]

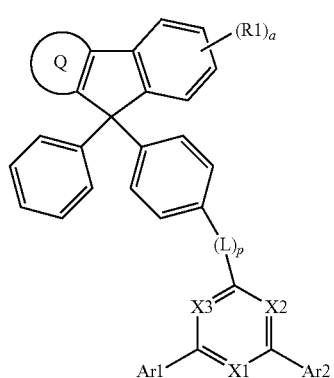

[Chemical Formula 4]

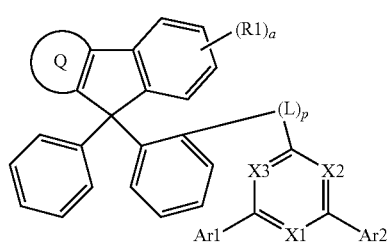

wherein in Chemical Formulae 2 to 4:

the definitions of Q, R1, L, X1 to X3, Ar1, Ar2, a, and p are the same as those defined in Chemical Formula 1.

3. The hetero-cyclic compound of claim 1, wherein Chemical Formula 1 is Chemical Formula 5:

[Chemical Formula 5]
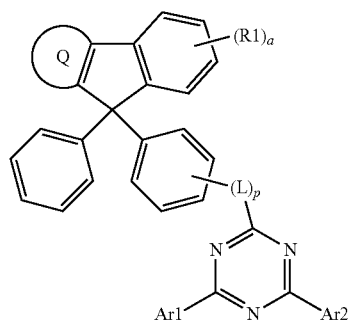
wherein in Chemical Formula 5,
the definitions of Q, R1, L, Ar1, Ar2, a, and p are the same as those defined in Chemical Formula 1.
4. A hetero-cyclic compound of any one of the following Chemical Formulae 6 to 11:
[Chemical Formula 6]
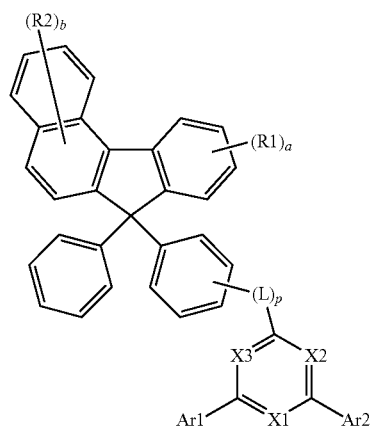
[Chemical Formula 7]
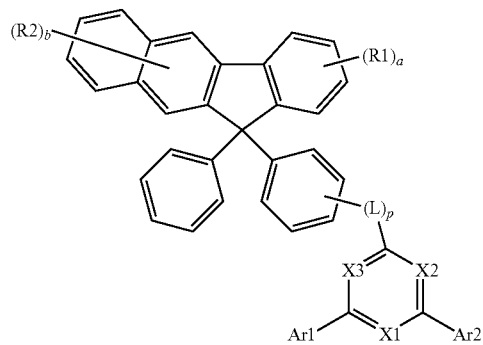
[Chemical Formula 8]
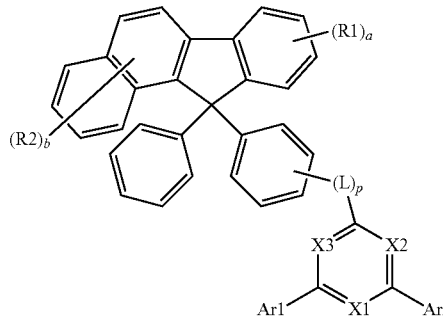
[Chemical Formula 9]
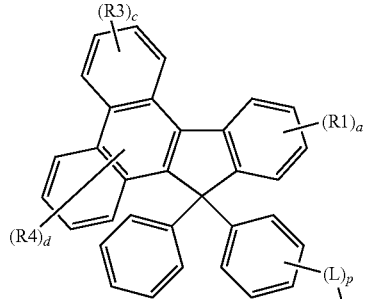
[Chemical Formula 10]
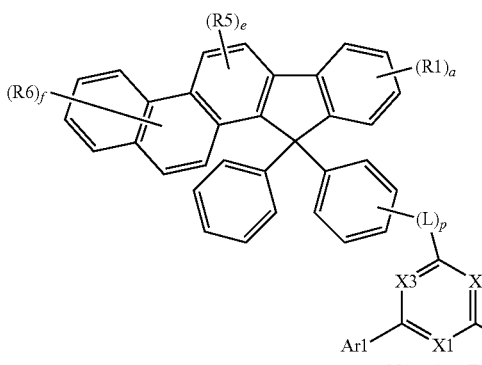
[Chemical Formula 11]
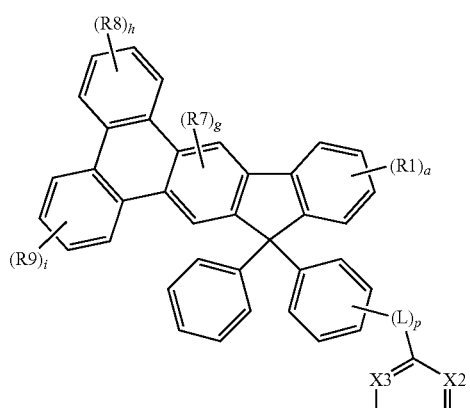

wherein in Chemical Formulae 6 to 11:
X1 to X3 are the same as or different from each other, and are each independently CR or N;
L is a direct bond, a substituted or unsubstituted arylene, or a substituted or unsubstituted heteroarylene;
R, R1, Ar1, and Ar2 are the same as or different from each other, and are each independently hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphine oxide group, a substituted or unsubstituted aryl group, or a substituted or unsubstituted hetero-cyclic group, or combine with an adjacent group to form a substituted or unsubstituted ring;
a is an integer of 0 to 4;
p is an integer of 0 to 5;
R2 to R9 are the same as or different from each other, and are each independently hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphine oxide group, a substituted or unsubstituted aryl group, or a substituted or unsubstituted hetero-cyclic group, or combine with an adjacent group to form a substituted or unsubstituted ring;
b and f are the same as or different from each other, and are each independently an integer of 0 to 6;
c, d, h, and i are the same as or different from each other, and are each independently an integer of 0 to 4;
e and g are the same as or different from each other, and are each independently an integer of 0 to 2; and
when a, p, b, c, d, e, f, g, h, and i are each 2 or more, the structures in the parenthesis are the same as or different from each other.

5. The hetero-cyclic compound of claim 1, wherein Chemical Formula 1 is Chemical Formula 12:

[Chemical Formula 12]

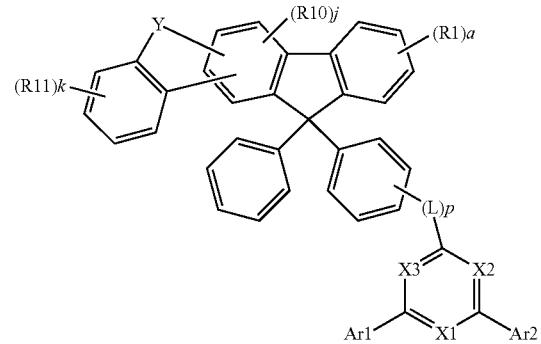

wherein in Chemical Formula 12,
the definitions of R1, L, X1 to X3, Ar1, Ar2, a, and p are the same as those defined in Chemical Formula 1;
Y is S, O, or NR;
R, R10, and R11 are the same as or different from each other, and are each independently hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphine oxide group, a substituted or unsubstituted aryl group, or a substituted or unsubstituted hetero-cyclic group, or combine with an adjacent group to form a substituted or unsubstituted ring;
j is an integer of 0 to 2;
k is an integer of 0 to 4; and
when j and k are each 2 or more, the structures in the parenthesis are the same as or different from each other.

6. The hetero-cyclic compound of claim 1, wherein Chemical Formula 1 is any one of the following Chemical Formulae 13 to 18:

[Chemical Formula 13]

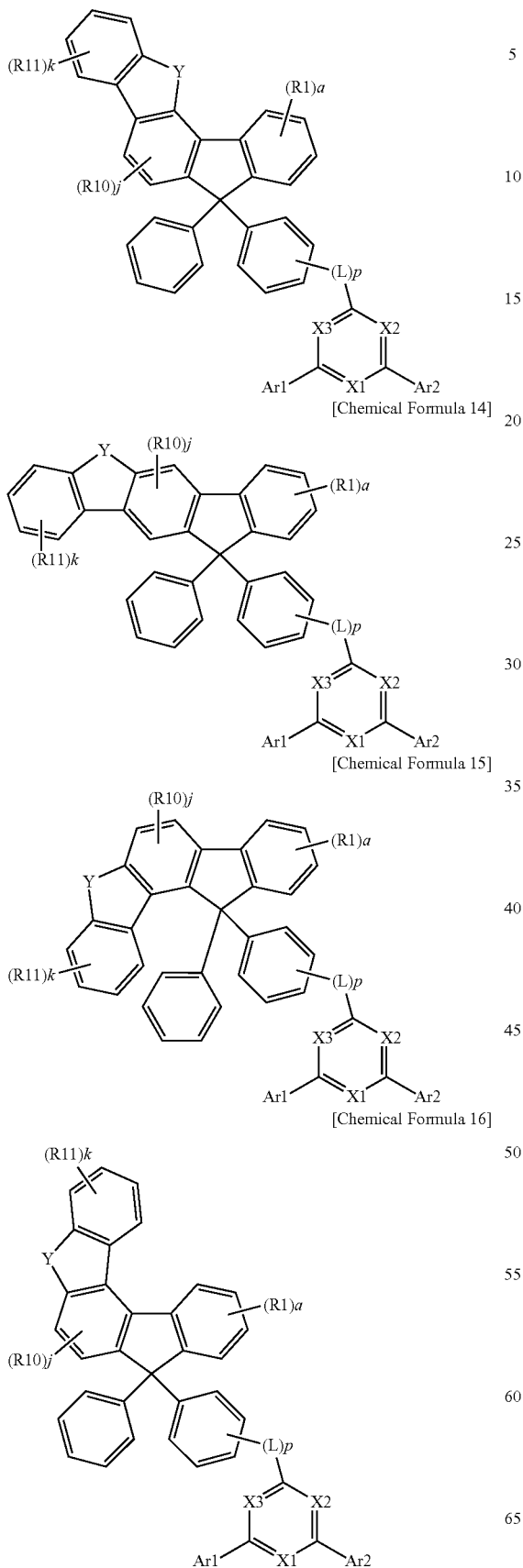

[Chemical Formula 14]

[Chemical Formula 15]

[Chemical Formula 16]

[Chemical Formula 17]

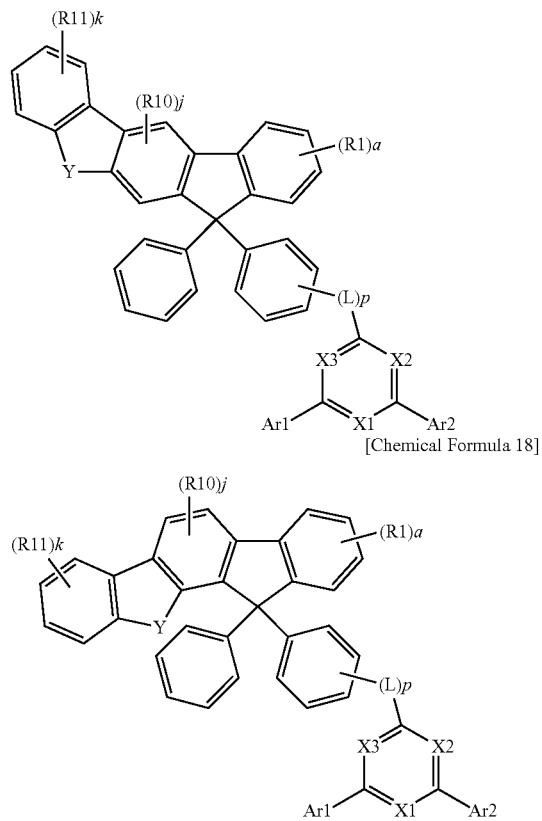

[Chemical Formula 18]

wherein in Chemical Formulae 13 to 18:
the definitions of R1, L, X1 to X3, Ar1, Ar2, a, and p are the same as those defined in Chemical Formula 1;
Y is S, O, or NR;
R, R10, and R11 are the same as or different from each other, and are each independently hydrogen, deuterium, a halogen group, a nitrile group, a nitro group, a hydroxy group, a carbonyl group, an ester group, an imide group, an amino group, a substituted or unsubstituted silyl group, a substituted or unsubstituted boron group, a substituted or unsubstituted alkyl group, a substituted or unsubstituted cycloalkyl group, a substituted or unsubstituted alkoxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted aralkyl group, a substituted or unsubstituted aralkenyl group, a substituted or unsubstituted alkylaryl group, a substituted or unsubstituted alkylamine group, a substituted or unsubstituted aralkylamine group, a substituted or unsubstituted heteroarylamine group, a substituted or unsubstituted arylamine group, a substituted or unsubstituted arylheteroarylamine group, a substituted or unsubstituted arylphosphine group, a substituted or unsubstituted phosphine oxide group, a substituted or unsubstituted aryl group, or a substituted or unsubstituted hetero-cyclic group, or combine with an adjacent group to form a substituted or unsubstituted ring;

j is an integer of 0 to 2;

k is an integer of 0 to 4; and when j and k are each 2 or more, the structures in the parenthesis are the same as or different from each other.

7. The hetero-cyclic compound of claim 1, wherein L is a direct bond or an arylene which is unsubstituted or substituted with one or more substituents selected from the group consisting of deuterium, a halogen group, an amino group, a nitrile group, a nitro group, an alkyl group, an alkenyl group, an alkoxy group, a cycloalkyl group, an aryl group, and a hetero-cyclic group.

8. The hetero-cyclic compound of claim 1, wherein Ar1 and Ar2 are the same as or different from each other, and are each independently a substituted or unsubstituted phenyl group.

9. The hetero-cyclic compound of claim 1, wherein the compound of Chemical Formula 1 is any one selected from the following compounds:

Compound 1

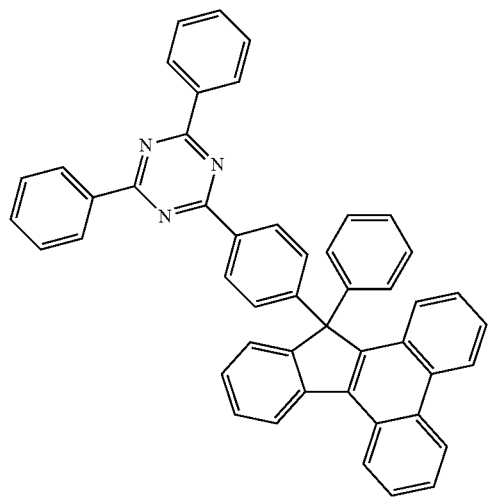

Compound 2

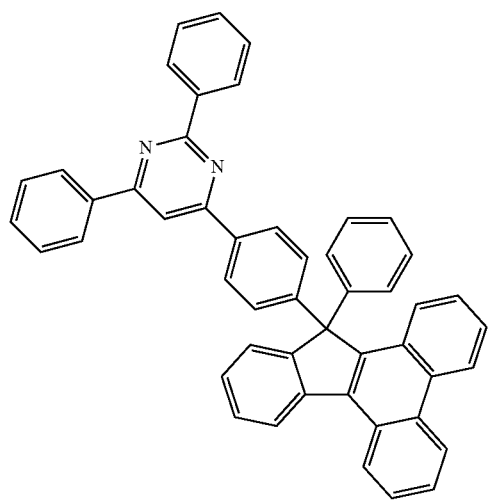

Compound 3

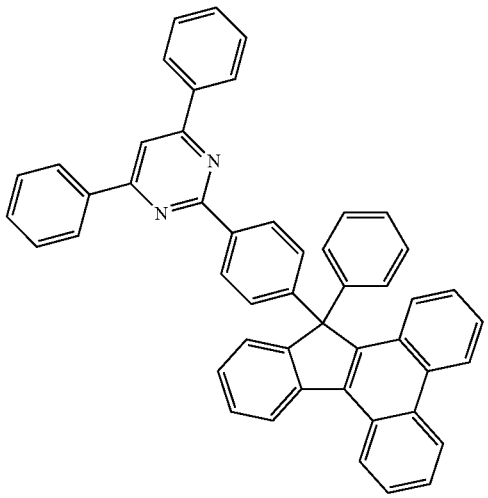

Compound 4

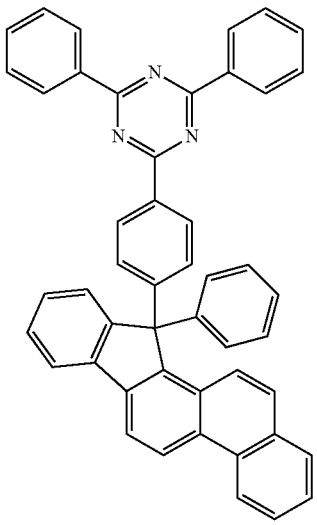

Compound 5

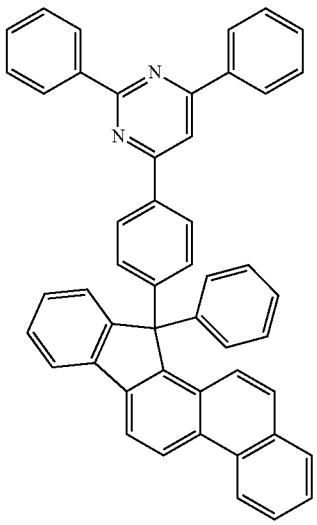

Compound 6
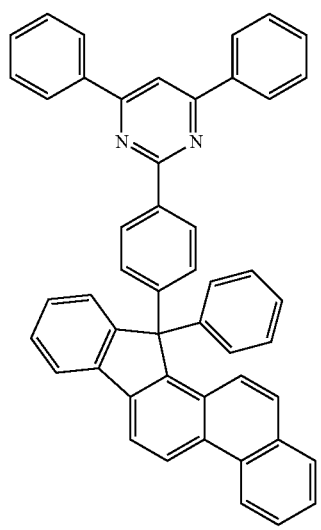
Compound 7
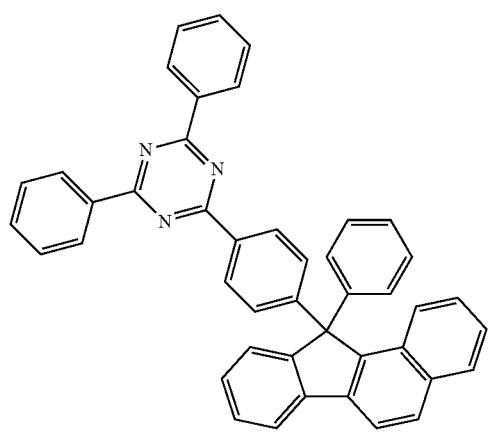
Compound 8
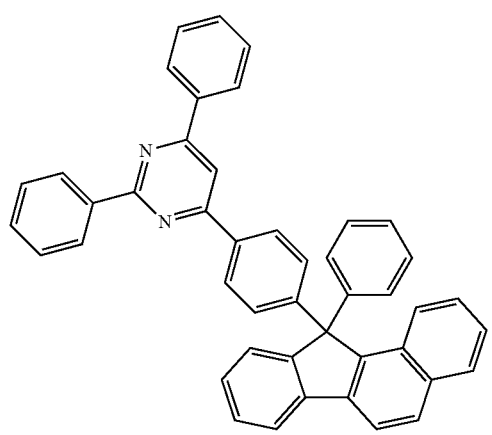
Compound 9
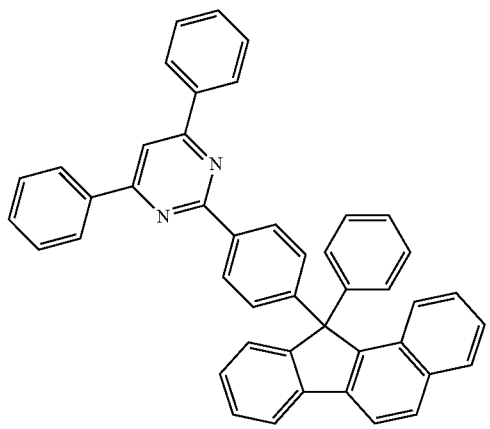
Compound 10
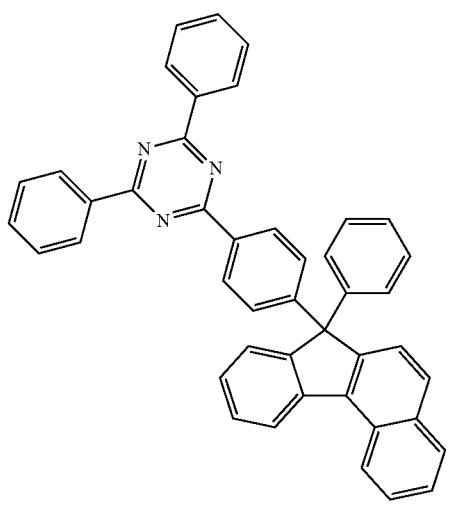
Compound 11
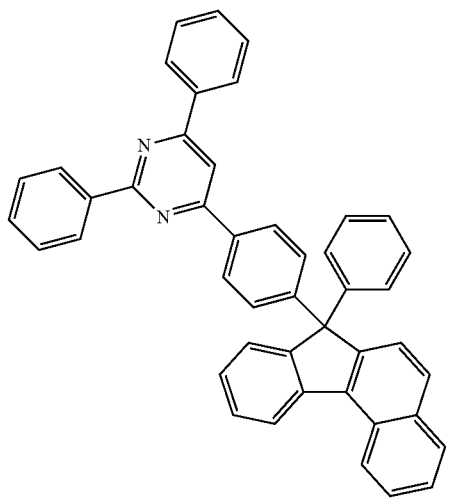

Compound 12
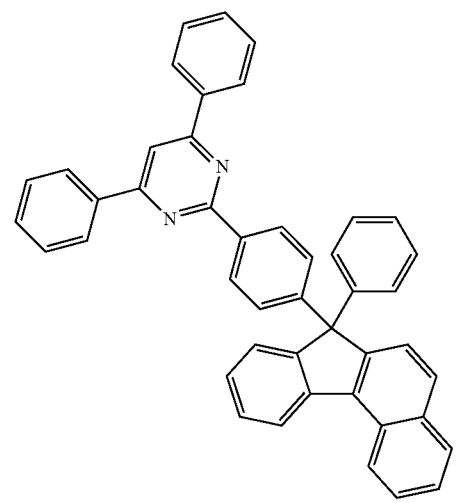
Compound 13
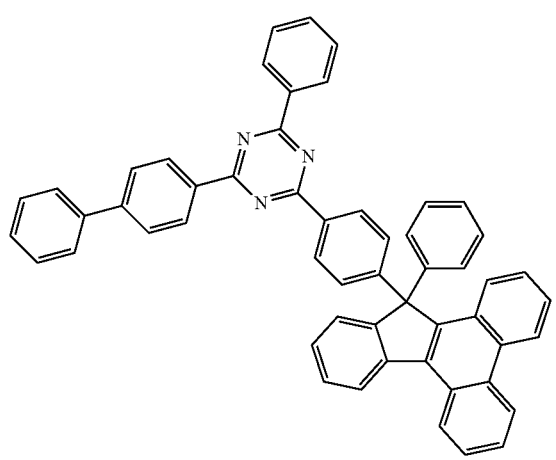
Compound 14
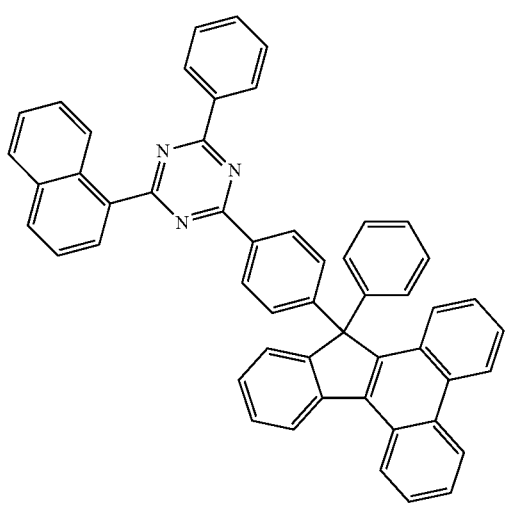
Compound 15
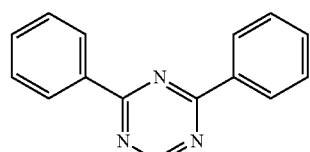
Compound 16
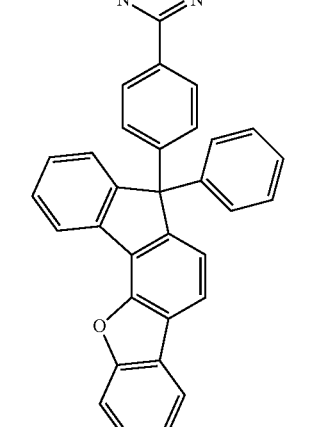
Compound 17
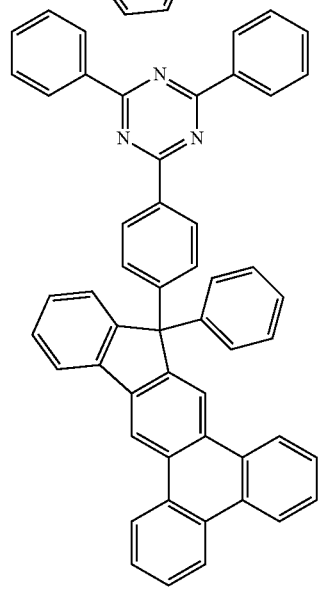

Compound 18
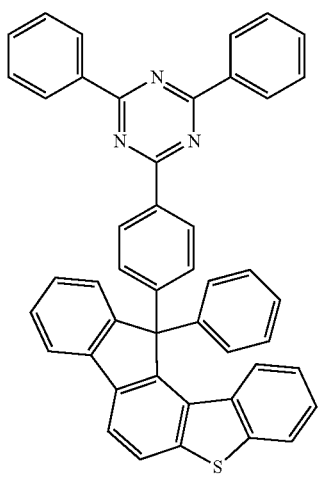
Compound 19
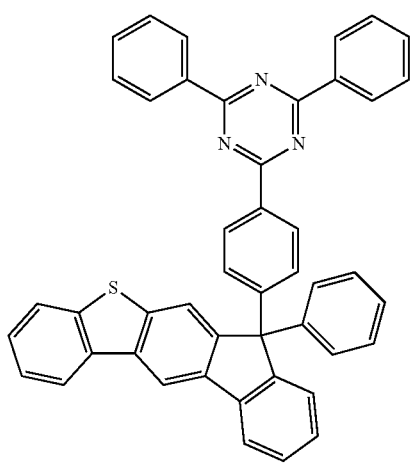
Compound 20
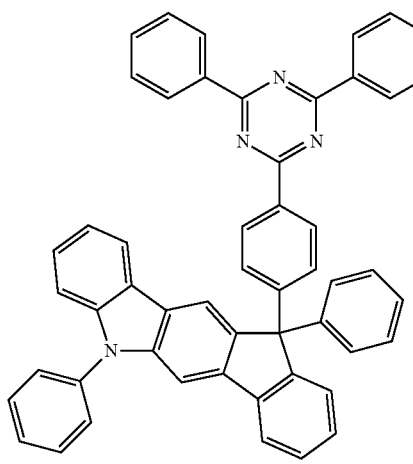
Compound 21
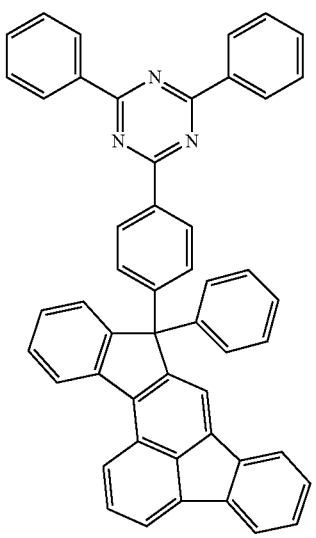
Compound 22
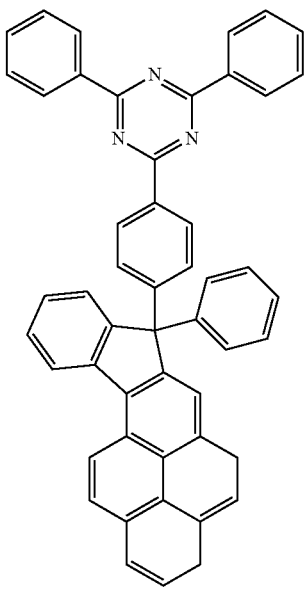
Compound 23
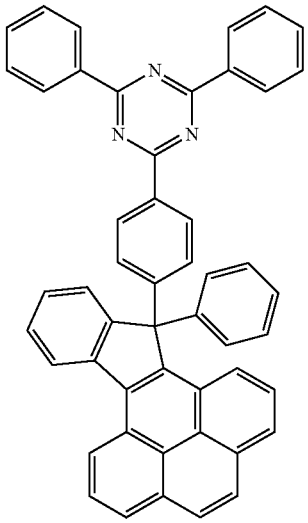

-continued
Compound 24
Compound 25
Compound 26
Compound 27
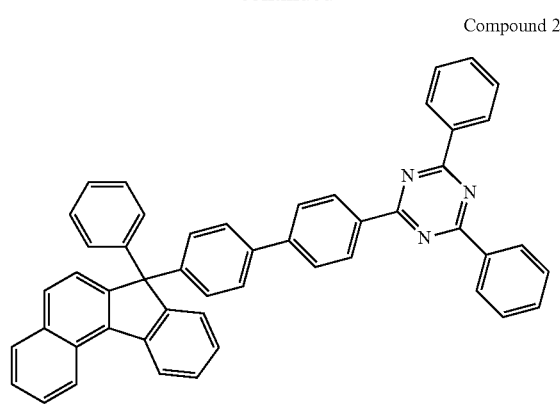
-continued
Compound 28
Compound 29
Compound 30
Compound 31
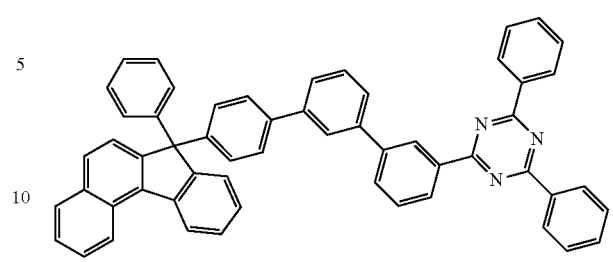
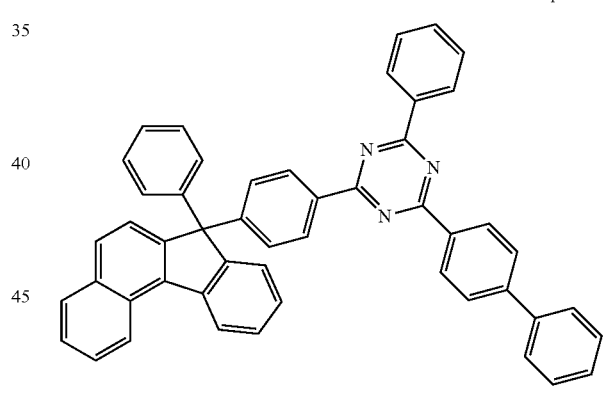
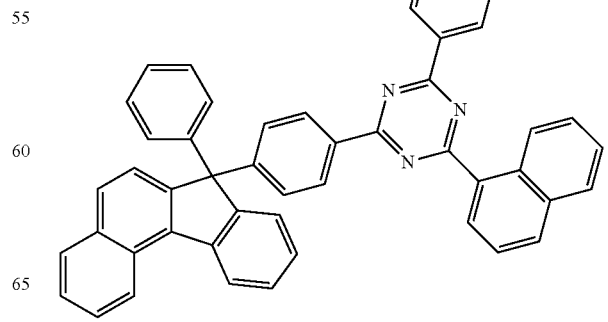

Compound 32

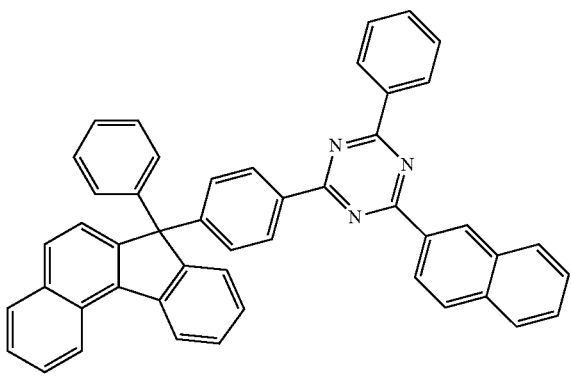

Compound 33

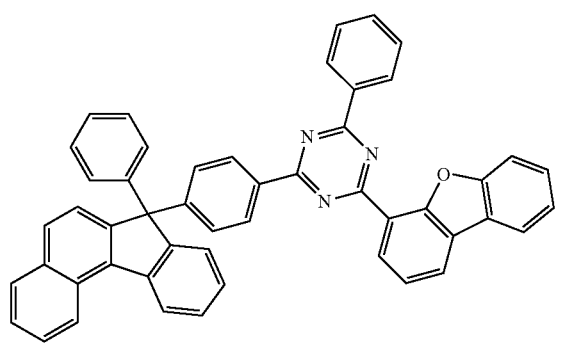

Compound 34

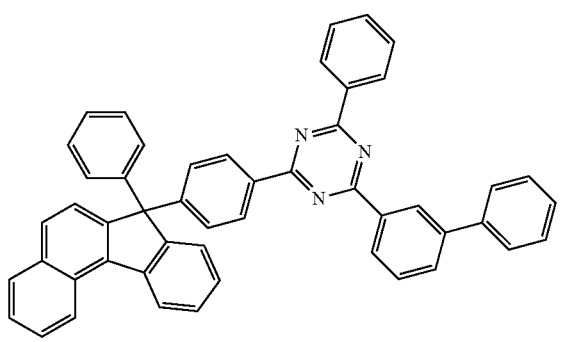

Compound 35

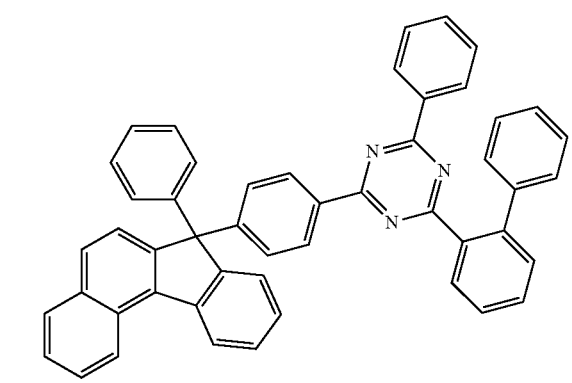

Compound 36

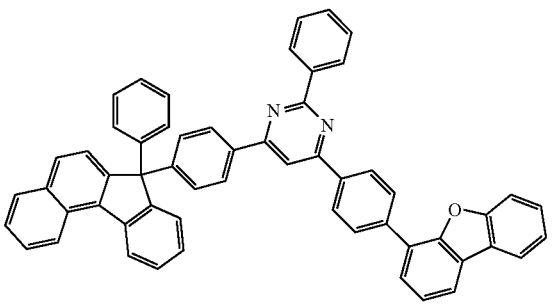

Compound 37

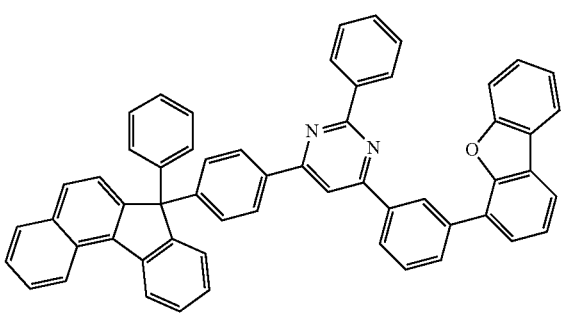

Compound 38

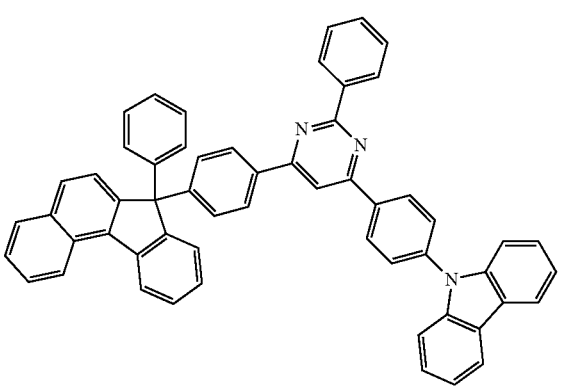

Compound 39

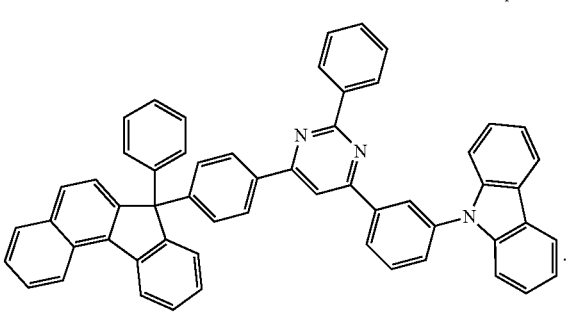

10. An organic light emitting device, comprising:
a first electrode;
a second electrode provided to face the first electrode; and
one or more organic material layers provided between the first electrode and the second electrode,
wherein one or more layers of the organic material layers comprise the hetero-cyclic compound of claim 1.

11. The organic light emitting device of claim 10, wherein the organic light emitting device comprises a structure of the following Chemical Formula 1-A as a material for a dopant of a light emitting layer of the organic material layers:

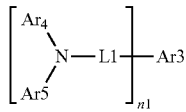

[Chemical Formula 1-A]

wherein in Chemical Formula 1-A:
- Ar3 is a substituted or unsubstituted benzofluorene group, a substituted or unsubstituted fluoranthene group, a substituted or unsubstituted pyrene group, or a substituted or unsubstituted chrysene group,
- L1 is a direct bond, a substituted or unsubstituted arylene group, or a substituted or unsubstituted heteroarylene group,
- Ar4 and Ar5 are the same as or different from each other, and are a substituted or unsubstituted aryl group, a substituted or unsubstituted silyl group, a substituted or unsubstituted alkyl group, a substituted or unsubstituted arylalkyl group, or a substituted or unsubstituted hetero-cyclic group;
- Ar4 and Ar5 optionally combine with each other to form a ring;
- n1 is an integer of 1 or more; and
- when n1 is 2 or more, the structures in the parenthesis are the same as or different from each other.

12. The organic light emitting device of claim 10, wherein the organic material layer comprising the hetero-cyclic compound is a hole injection layer, a hole transporting layer, or a layer which simultaneously injects and transports holes.

13. The organic light emitting device of claim 10, wherein the organic material layer comprising the hetero-cyclic compound is an electron injection layer, an electron transporting layer, or a layer which simultaneously injects and transports electrons.

14. The organic light emitting device of claim 10, wherein the organic material layer comprising the hetero-cyclic compound is a light emitting layer.

15. The hetero-cyclic compound of claim 1, wherein Ar1 and Ar2 are the same as or different from each other, and each independently is an aryl group, a hetero-cyclic group, or combine with an adjacent group to form a substituted or unsubstituted ring.

* * * * *

UNITED STATES PATENT AND TRADEMARK OFFICE
CERTIFICATE OF CORRECTION

PATENT NO. : 10,745,362 B2
APPLICATION NO. : 15/567276
DATED : August 18, 2020
INVENTOR(S) : Min Woo Jung et al.

Page 1 of 1

It is certified that error appears in the above-identified patent and that said Letters Patent is hereby corrected as shown below:

On the Title Page

In Item (72) Inventors, left column, fifth line, please replace the inventor's name "Dong Heo" with — Dong Uk HEO —

In the Claims

In Claim 2 at Column 66, Lines 10-25, [Chemical Formula 2] should appear as follows:

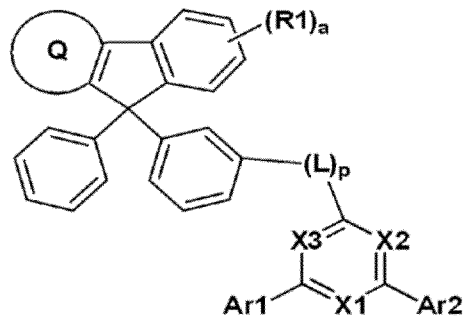

Signed and Sealed this
Fifteenth Day of September, 2020

Andrei Iancu
*Director of the United States Patent and Trademark Office*